United States Patent [19]
Voda

[11] Patent Number: 6,110,163
[45] Date of Patent: Aug. 29, 2000

[54] PREFORMED CORONARY ARTERY GUIDE CATHETER

[76] Inventor: Jan Voda, 1404 Camden Way, Oklahoma City, Okla. 73116

[21] Appl. No.: 09/235,077

[22] Filed: Jan. 21, 1999

Related U.S. Application Data

[62] Division of application No. 08/926,129, Sep. 9, 1997, Pat. No. 5,868,700, which is a continuation of application No. 08/558,006, Nov. 13, 1995, which is a continuation of application No. 08/190,149, filed as application No. PCT/US93/04031, Apr. 29, 1993, abandoned, which is a continuation-in-part of application No. 07/877,288, May 1, 1992, Pat. No. 5,306,263.

[51] Int. Cl.$^7$ ................................................. A61M 25/00
[52] U.S. Cl. .......................... 604/523; 604/532; 604/534
[58] Field of Search ................................... 604/523, 525, 604/530, 532, 533, 534, 264, 500

[56] References Cited

U.S. PATENT DOCUMENTS

| | | | |
|---|---|---|---|
| 4,020,829 | 5/1977 | Willson et al. | 128/2 M |
| 4,033,331 | 7/1977 | Guss et al. | 128/2 M |
| 4,117,836 | 10/1978 | Erikson | 128/2.05 R |
| 4,292,976 | 10/1981 | Banka | 128/656 |
| 4,547,193 | 10/1985 | Rydell | 604/282 |
| 4,568,338 | 2/1986 | Todd | 604/281 |
| 4,738,667 | 4/1988 | Galloway | 604/281 |
| 4,747,840 | 5/1988 | Ladika et al. | 604/280 |
| 4,784,639 | 11/1988 | Patel | 604/53 |
| 4,822,345 | 4/1989 | Danforth | 604/282 |
| 4,909,787 | 3/1990 | Danforth | 604/95 |
| 4,925,445 | 5/1990 | Sakamoto et al. | 604/95 |
| 4,935,004 | 6/1990 | Cruz | 604/29 |
| 4,950,228 | 8/1990 | Knapp, Jr. et al. | 604/8 |
| 4,976,691 | 12/1990 | Sahota | 604/96 |
| 4,981,477 | 1/1991 | Schon et al. | 604/264 |
| 5,044,369 | 9/1991 | Sahota | 128/658 |
| 5,045,072 | 9/1991 | Castillo et al. | 604/280 |
| 5,098,412 | 3/1992 | Shiu | 604/280 |
| 5,195,990 | 3/1993 | Weldon | 604/281 |
| 5,215,540 | 6/1993 | Anderhub | 604/281 |
| 5,306,263 | 4/1994 | Voda | 604/281 |
| 5,401,258 | 3/1995 | Voda | 604/281 |

FOREIGN PATENT DOCUMENTS

| | | |
|---|---|---|
| 0 132 344 A2 | 1/1985 | European Pat. Off. . |
| 0 256 478 A1 | 2/1988 | European Pat. Off. . |
| 0 277 366 A1 | 8/1988 | European Pat. Off. . |
| 0 323 738 A2 | 7/1989 | European Pat. Off. . |
| WO 92/12754 | 8/1992 | WIPO . |

OTHER PUBLICATIONS

USCI Block™ Right Coronary Guiding Catheter, 1989, 2 pages.

USCI Video Tape ("Select Curve Guiding Catheter: Cannulating the Right Coronary Artery") transcript and selected figures, 1988.

USCI Video Tape: Select Curve Guiding Catheter: Cannulating the Right Coronary Artery, USCI, C.R. Bard, 1988.

USCI "Positrol II and Nycore™ Cardiovascular Catheter" pp. 1–21.

Amplatz, K., et al. Mechanics of Selective Coronary Artery Catherization via Femoral Approach, Radiology 89: 1040–1047, Dec. 1967.

Judkins, M., Percutaneous Transfemoral Selective Coronary Arteriography, Radiologic Clinics of North America—vol. VI, No. 3, Dec. 1968, pp. 467–492.

Carr, M., The Use of the Guiding Catheter in Coronary Angioplasty: The Technique of Manipulating Catheters to Obtain the Necessary Power to Cross Tight Coronary Stenoses, Catheterization and Cardiovascular Diagnosis 12: 189–197, 1986.

(List continued on next page.)

*Primary Examiner*—John D. Yasko
*Attorney, Agent, or Firm*—Crompton, Seager & Tufte, LLC

[57] ABSTRACT

A catheter having an elongate body including a central lumen adapted to slidably receive a therapeutic catheter. The catheter includes a soft tip adapted to lodge in the ostium of the right coronary artery. The elongate body is formed near the distal end to impinge against the wall of the aorta opposite the ostium of the coronary artery.

1 Claim, 24 Drawing Sheets

OTHER PUBLICATIONS

Bourassa "Cardiovascular Catheters Sterile" brochure, Jun., 1972, 4 pages.

Arani STE: A New Catheter for Angioplasty of the Right Coronary Artery and Aortocoronary Bypass Grafts, Cath. Cardiovasc. Diagn. 11:647–653, 1985.

Block, PC et al.: PTCA in Perspective, USCI Division, C.R. Bard, Inc. Billerica MA, pp. 23–42, 1986.

Wilson et al., Biplane Selective Coronary Arteriography Via Percutaneous Transfemoral Approach, presented at the Sixty–Seventh Annual Meeting of the American Roentgen Ray Society, San Francisco, California, Sep. 27–30, 1966.

El Gamal et al., Improved Success Rate of Percutaneous Transluminal Graft and Coronary Angioplasty with the El Gamal Guiding Catheter, Catherization and Cardiovascular Diagnosis, 11:89–96 (1985).

SciMed Life Systems, Inc. Guide Catheter Training, 1990.

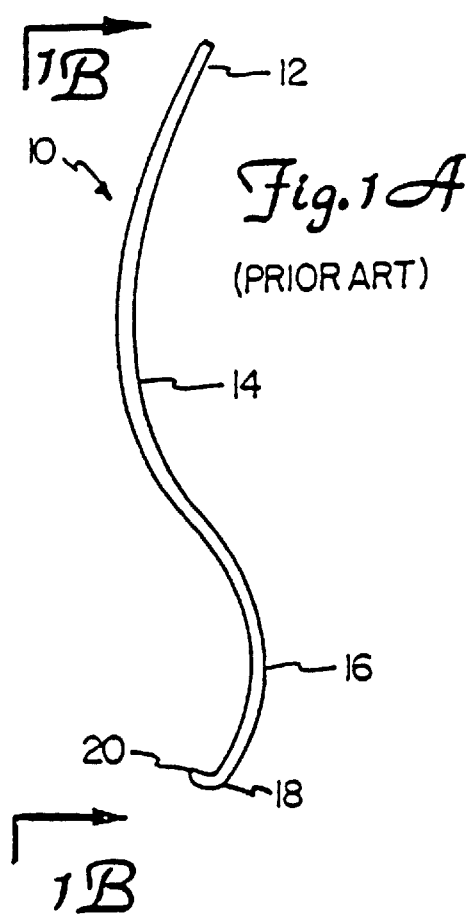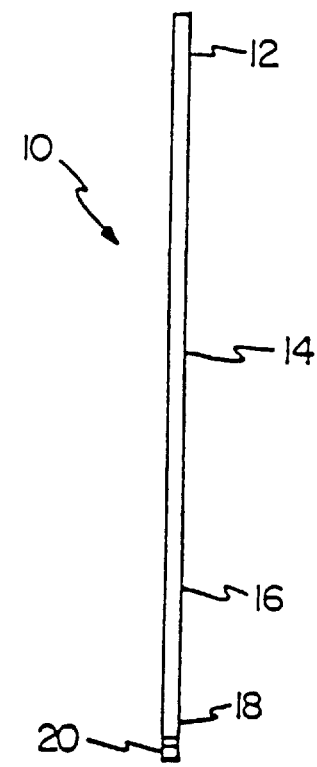
Fig. 1A (PRIOR ART)
Fig. 1B (PRIOR ART)

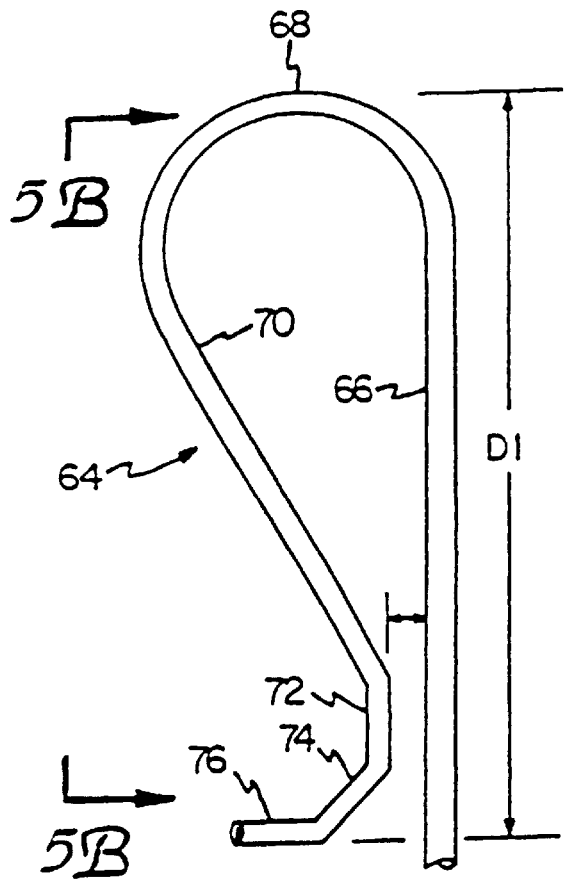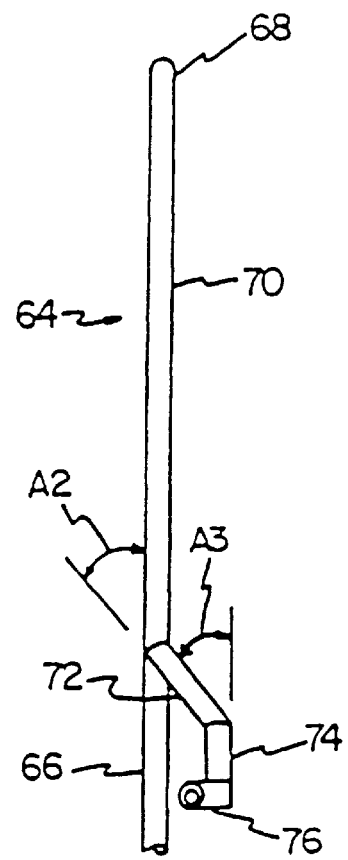
Fig. 5A
Fig. 5B

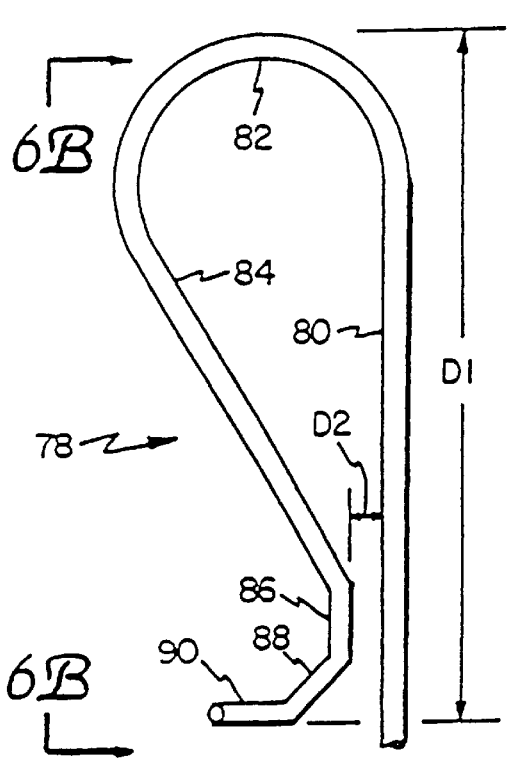
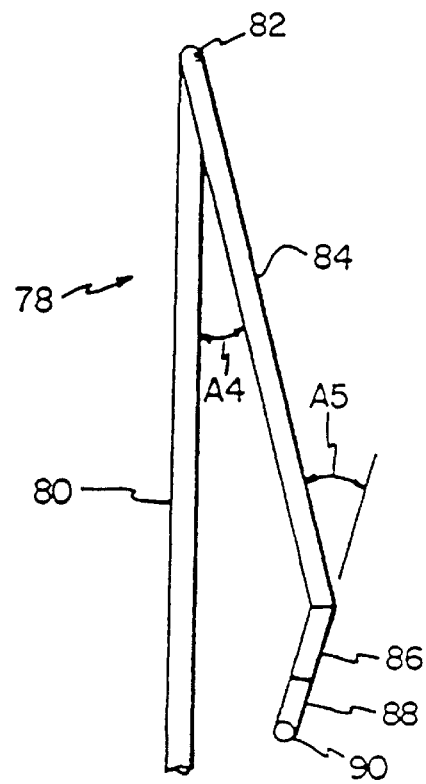
Fig. 6A
Fig. 6B

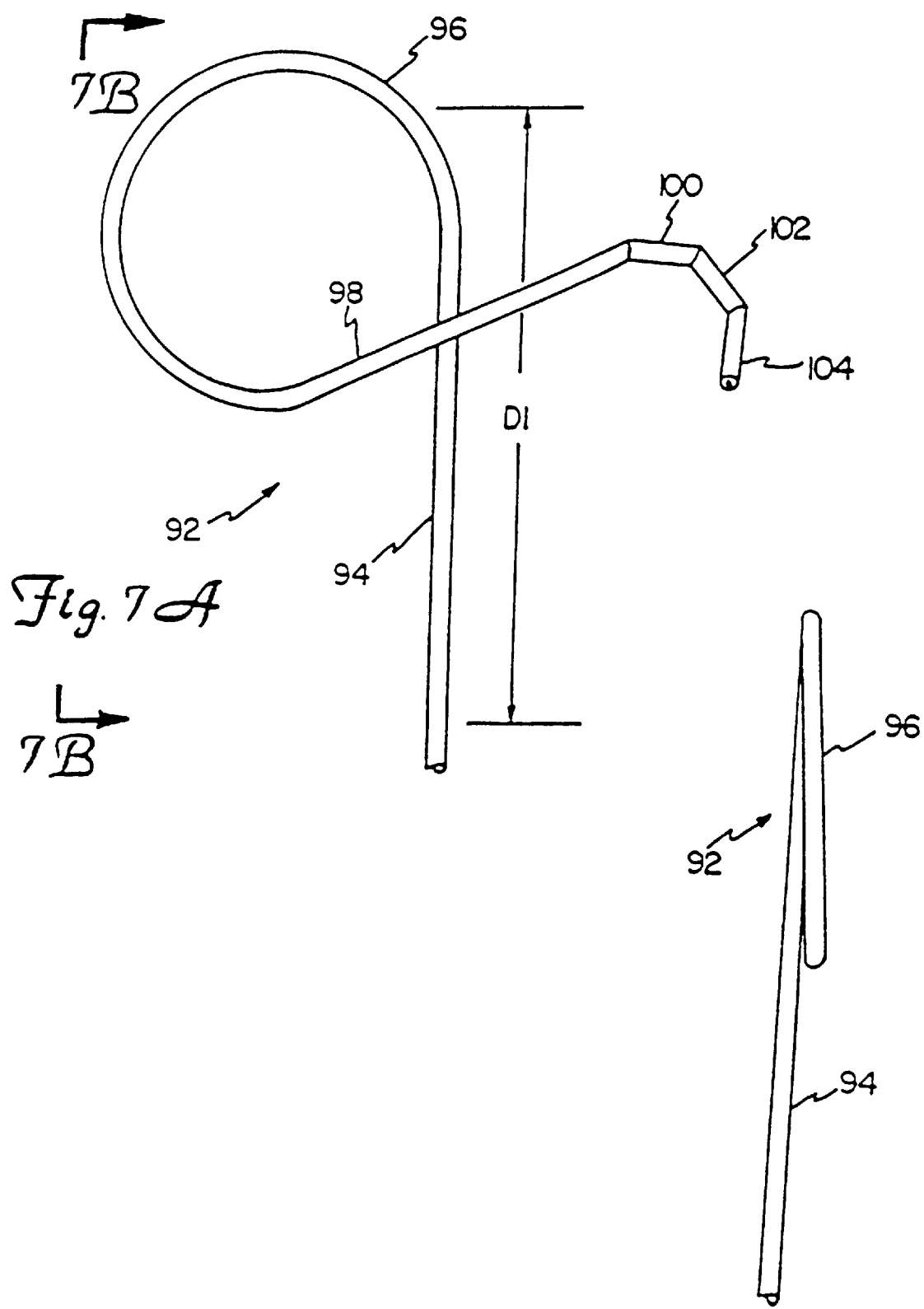

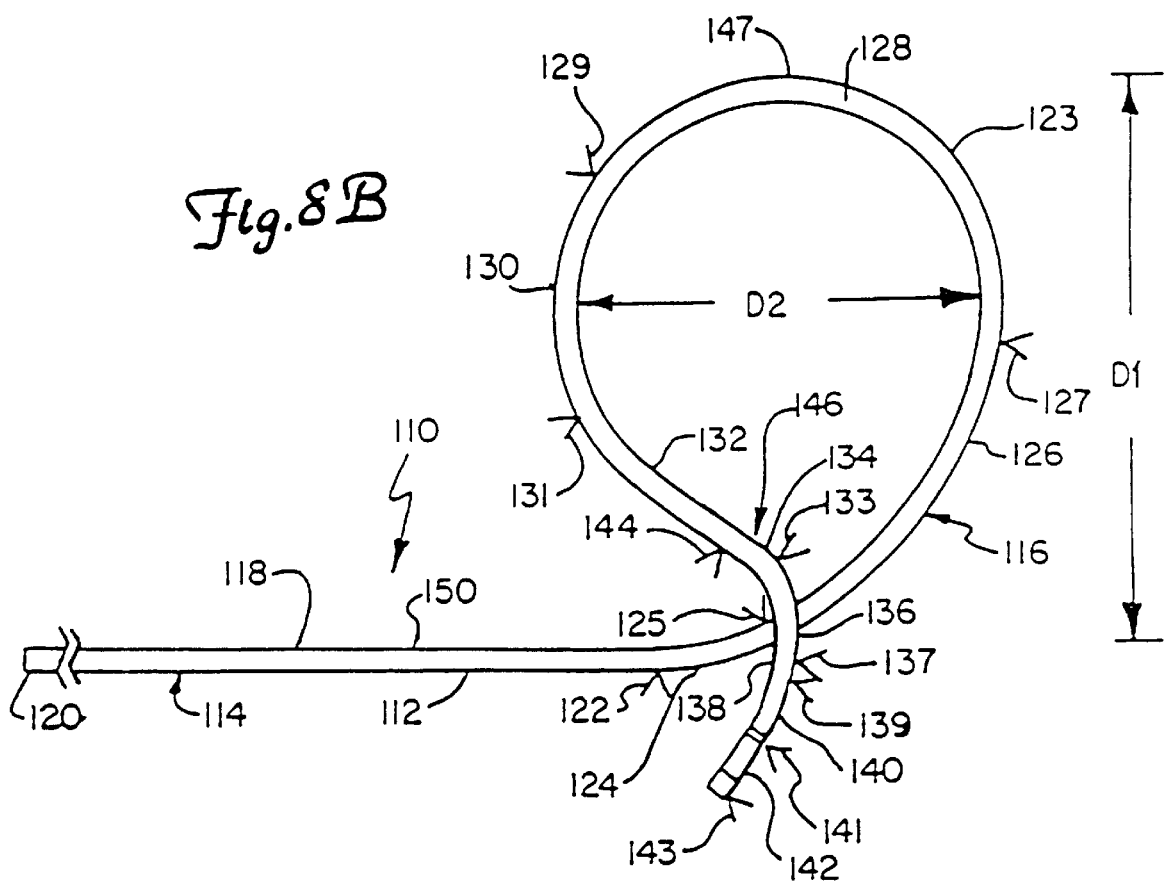

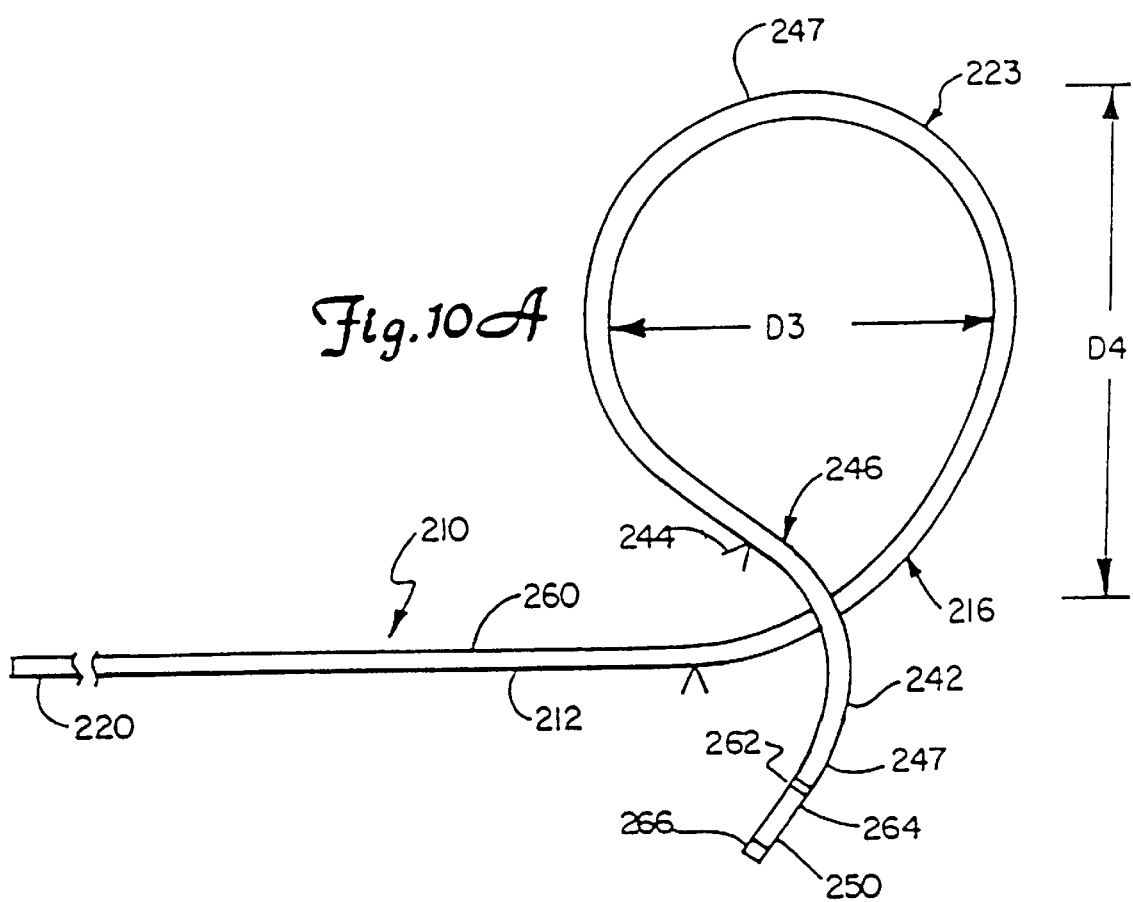

PREFORMED CORONARY ARTERY GUIDE
CATHETER

This application is a divisional of application Ser. No. 08/926,129, filed Sep. 9, 1997, now U.S. Pat. No. 5,868,700 which in turn is a continuation of application Ser. No. 08/558,006, filed Nov. 13, 1995 pending, which in turn is a continuation of application Ser. No. 08/190,149, filed Feb. 4, 1994, now abandoned which in turn is a Rule 371 National Phase Filing of PCT/US93/04031, with an International Filing Date of Apr. 29, 1993, which in turn is a continuation-in-part of application Ser. No. 07/877,288, filed May 1, 1992, now U.S. Pat. No. 5,306,263.

BACKGROUND OF THE INVENTION

This invention relates generally to catheters adapted to be inserted into the cardiovascular system of a living body and, more particularly, to a preshaped catheter having an improved distal end portion for providing more precise access to the right main coronary artery of the cardiovascular system.

Catheters are often used in the performance of medical procedures such as coronary angiography for injecting dye, or the like, into the cardiovascular system for diagnosis; and angioplasty to widen the lumen of a coronary artery which has become at least partially blocked by a stenotic lesion causing an abnormal narrowing of the artery due to injury or disease. In these techniques the distal end of a therapeutic catheter is introduced into the aorta by way of the femoral artery. The proximal end of the catheter is then manipulated so its distal end is inserted into the lumen of a selected coronary artery branching off from the aorta. A typical treatment procedure would involve initially inserting a guiding catheter into the cardiovascular system in the above manner, followed by the introduction of a suitable therapeutic device, such as a dilating catheter, a laser catheter, an atherectomy catheter, or the like. The therapeutic catheter is guided through the guiding catheter until its distal end portion is positioned adjacent the stenotic lesion in the coronary artery for use in reducing the blockage in the artery. In all such medical procedures, it is absolutely essential that the guiding catheter has the appropriate shape for proper alignment of its distal end relative to the coronary artery.

The most common catheter used in treatment of the right main coronary artery is what is often referred to as a "Judkins" catheter, which has a specially shaped distal end portion for facilitating insertion and engagement into the right coronary artery. However, there are some significant disadvantages to the "Judkins" catheter, such as its frequent inability to align perfectly coaxially with the selected artery and thus permit optimal treatment, and its inability to adequately support other therapeutic devices such as balloon catheters. Also, the Judkins catheter requires a 180 degree rotation and adroit manipulation to selectively engage its distal end in the right main coronary artery, which makes it more difficult to use effectively and efficiently.

In FIGS. 1A and 1B of the drawings, the reference numerical 10 refers, in general, to a well known prior art catheter, commonly referred to as a "Judkins" catheter. The catheter 10 is in the form of an elongated tubular member having a straight portion 12 (shown partially in FIGS. 1A and 1B) and a distal end portion. The distal end portion consists of a tertiary curved portion 14, a secondary curved portion 16, a primary curved portion 18, and a tip portion 20. The tertiary curved portion 14 extends from the straight portion 12 and is bent to form a curve of approximately 30°. The secondary curved portion 16 extends from the tertiary curved portion 14 and is bent in the opposite direction to the tertiary curved portion 14 to form a curve of approximately 30°. The primary curved portion 18 extends from the curved portion 16 and is bent to form a curve of approximately 90° and the tip portion 20 extends from the curved portion 18. According to a typical Judkins catheter the curved portions 14 and 16 would have a radius of curvature of 10 and 5 centimeters ("cm."), respectively, and the tip portion 20 would have a length of 1 cm. The catheter 10 is usually fabricated of a plastic material selected to exhibit flexibility and softness yet permit adequate "torque control" (i.e., the ability to transmit twisting forces along its length) so that it can be located and maneuvered precisely within a cardiovascular system by skilled manipulation of its proximal end, as will be described.

A typical cardiovascular system is shown in FIGS. 1C and 1D and is referred to, in general, by the reference numeral 22. The system 22 includes an aorta 24 comprised of a descending aorta 24a, an ascending aorta 24b, and an aortic arch 24c which extends from the descending aorta 24a to the ascending aorta 24b over a curve of approximately 180°. The ascending aorta 24b then branches through a right ostium 26 and a left ostium 27 into a right coronary artery 28 and a left coronary artery 30, respectively. An aortic valve 32 extends between the right coronary artery 28 and the left coronary artery 30 and is connected to the heart (not shown). As better shown in FIG. 1D, the right coronary artery 28 and the left coronary artery 30 are normally angularly spaced approximately 120°.

The prior art Judkins catheter 10 of FIGS. 1A and 1B is designed for use as a diagnostic catheter in the right coronary artery 28 but is also used as a guiding catheter for treatment of stenotic lesions, or the like. To this end, the catheter 10 is inserted into the system 22 and is manipulated so that, ideally, the tip portion 20 of the catheter 10 is positioned through the ostium 26 and into the lumen of the right coronary artery 28 and used to guide other therapeutic devices such as balloon, laser or atherectomy catheters, or the like (not shown) into the right coronary artery 28.

To assist in advancing the catheter 10 through the system 22, a relatively stiff wire is initially inserted into the catheter 10 to straighten it. After the catheter is inserted into the ascending aorta 24b, the wire is withdrawn, causing the catheter to position itself along the wall of the ascending aorta 24b, 1 to 2 cm. above the ostium 27 of the left coronary artery 30. As a result, the tip portion 20 of the Judkins catheter 10 points away from the ostium 26 of the right coronary artery 28 and must be rotated 180°. During this rotation, the catheter 10 will suddenly descend about 3 cm. until the tip portion 20 hopefully aligns with the ostium 26 of the right coronary artery 28 in a coaxial relationship as shown in FIG. 1C.

However, due to the particular configuration of the Judkins catheter 10, the tip portion 20 is often misaligned with the ostium 26 of the right coronary artery 28 and is not located coaxially with the latter artery. Thus, when an inner catheter or therapeutic device such as a balloon catheter (not shown) is passed through the catheter 10, the former often strikes the wall of the ascending aorta 24b or the right coronary artery 28 increasing the risk of damage. Also, due to the fact that the curved portion 18 is positioned adjacent to the wall of the ascending aorta 24b which contains the ostium 26 of the right coronary artery 28 and is a considerable distance from the wall of the ascending aorta 24b opposite the ostium 26, the catheter 10 does not provide support for other catheters or devices that are passed through the catheter 10. This problem is described in depth in Danforth U.S. Pat. No. 4,909,787. Due to the lack of support, when axial forces are exerted on the tip portion 20, such as when a dilation balloon is advanced, the tip portion 20 has a tendency to push back from the ostium 26 causing the tip portion 20 to dislodge from the lumen of the right coronary artery 28 and the therapeutic device to prolapse in the ascending aorta 24b. Thus, the therapeutic device loses its preferred orientation within the ascending aorta and right coronary artery. After this occurs, further advancement of the therapeutic device becomes nearly impossible because the Judkins catheter no long provides adequate support to the highly flexible shaft of the therapeutic device as one attempts to push the therapeutic device across the tight stenosis.

The lack of "backup" support happens because the Judkins catheter was not originally intended to serve as a conduit for other therapeutic devices into a patient's arterial system. Rather, the Judkins catheter was designed and configured merely to provide a means for introducing contrast fluid into the aortic root and main coronary artery region.

Various attempts to address these problems are described in the prior art. One of these attempted solutions is the Arani Double Loop guiding catheter. This catheter is illustrated and described in Arani, A New Catheter For Angioplasty of the Right Coronary Artery and Aorto-Coronary Bypass Grafts, Catheterization and Cardiovascular Diagnosis 11:647–653 (1985) and in a videotape publication, Select Curve Guiding Catheters: Cannulating the Right Coronary Artery, USCI/C.R. BARD (1988).

In FIGS. 2A, 2B and 2C, the Arani-type Double Loop guide catheter for the right coronary artery is presented to illustrate its use and the attendant difficulties and deficiencies of the Arani-type catheters for catheterization of the right coronary artery when used for angioplasty.

The Arani catheter is shown in FIG. 2A in a relaxed or "equilibrium" state prior to insertion into the cardiovascular system. The Arani-type Double Loop guide catheter includes a first straight proximal portion 402, a secondary curve portion 404, a second straight distal portion 406, a primary curve portion 408, and a distal tip straight portion 410 having a tip 412.

The Arani-type Double Loop catheter 400 is shown disposed in a cardiovascular system 500 from a left anterior oblique (LAO) view as seen under fluoroscopy by the physician as shown in FIGS. 2B and 2C. The cardiovascular system includes a descending aorta 502, an aortic arch 504, and head and neck vessels 506 extending from a roof 508 of the aortic arch 504. The aortic arch also has a floor 510. The cardiovascular system 500 further includes an ascending aorta 512 having an antero-lateral wall 514 and a postero-medial wall 516. A right main coronary artery 518 extends from the antero-lateral wall 514 of the ascending aorta and has an ostium 520 defining the interface between the ascending aorta 512 and the right coronary artery 518. A left main coronary artery 522 extends from the opposite wall of the ascending aorta 512 and has an ostium 524. A Sinus of Valsalva 526 extends below both the ostia of the left and right coronary arteries. The Sinus of Valsalva defines an area behind each cusp of the aortic valves where the aortic vessel wall bulges outward, forming a pouch-like dilatation. The Sinus of Valsalva 526 has a diameter wider than the diameter of the ascending aorta and have a wall having a curvature greater than that of the ascending aorta.

For use, the Arani catheter 400 must be first be maneuvered into the aortic complex. This is accomplished by advancing the catheter 400 over a stiff guide wire into the ascending aorta 412 to prevent the tip 412 from entering the great neck arteries. After removing the guide wire, the tip 412 typically is positioned against the antero-lateral wall 514 of the ascending aorta 512. With some downward or upward movement, the tip 412 will usually enter the ostium 520 of the right main coronary artery 518. As seen in FIG. 2B, the tip 412 of the Arani catheter 400 is marginally intubated into the ostium 520 of the right coronary artery 518.

The Arani catheter offers two ways to use the catheter to get backup support. The first way is the "fulcrum position" (FIG. 2B) where the tip of the Arani catheter is intubated into the ostium of the right coronary artery and a portion of the straight arm of the catheter is anchored against the opposite ascending aortic wall. The second way is the "buttressed position" (FIG. 2C) where the tip of the Arani catheter is positioned in the ostium of the right coronary artery, and then the catheter is advanced distally so that the secondary curve of the catheter contacts the antero-lateral wall of the aorta. As seen in FIG. 2B, the fulcrum position is achieved by pulling the catheter 400 proximally backward, with the tip 412 engaged in the ostium 520, so that the straight portion 406 of the catheter 400 contacts the postero-medial wall 516 of the ascending aorta 512. In addition, a more proximal portion of the catheter (the first straight proximal portion 402) contacts some portion of the wall (floor) of the proximal portion of the aortic arch 510. In this fulcrum position, the Arani catheter 400 attempts to provide backup support by gaining leverage off the postero-medial wall 516 of the ascending aorta. This leverage is created by pulling proximally backward on the catheter 400 which causes the tip 412 of the catheter 400 to tend to further seek the ostium 520. This leveraging is intended to counter stenotic pushback forces acting to push the tip 412 out of engagement with the ostium 520 of the right coronary artery 518.

However, the Arani catheter 400 when used in the fulcrum position has several major disadvantages. First, the Arani catheter 400 as used in the fulcrum position lacks stability. The catheter is limited from making substantially contiguous contact with the postero-medial wall 516 of the ascending aorta 512 and the inner wall (floor 510) of the aortic arch 504 throughout its length because the 90° secondary curve portion 404 forms such a relatively sharp bend in the catheter. This lack of contact created by the sharp bend provides less frictional engagement for the catheter to resist slippage when countering stenotic pushback forces. Second, this relatively sharp secondary curve of the catheter 400 in use inhibits achieving a direct and positive correspondence between advancement of the proximal end of the catheter and advancement of the tip 412 of the catheter into the ostium. This relatively severe bend retained in the catheter 400 in use distorts the 1:1 tip response that might otherwise occur in a catheter with relatively smooth curves along its entire length, from the proximal end to the distal end.

A third major disadvantage of using the Arani catheter in the fulcrum position is a lack of direct superior backup support which is created by negative correspondence between advancement of the proximal end of catheter and advancement of tip of catheter. As the Arani catheter 400 is moved into the fulcrum position, the tip moves distally forward but the heel (the proximal end of the primary curve of the catheter) moves away from a distal portion 517 of the postero-medial wall 516 of the ascending aorta to hang suspended in the ascending aorta adjacent the ostium 524 of the left coronary artery 522. This negative correspondence between advancement of the catheter's proximal end and the catheter's tip is a result of the fulcrum effect created by the balancing of the straight segment on the postero-medial wall 516. Moreover, in this fulcrum position the tip 412 can prolapse, i.e., become disengaged from the ostium 520, because there is no direct support because of the lack of contact between the heel of the catheter 400 and the distal portion 517 of the postero-medial wall 516 of the ascending aorta 512. Accordingly, when a tight stenosis is encountered during angioplasty, the stenotic pushback forces can overcome the countering forces provided by the fulcrum effect of the Arani-type catheter 400.

Thus, although one can achieve and maintain deeper coaxial intubation of the tip of the Arani catheter 400 using the fulcrum technique, one sacrifices backup support because the catheter will react by moving the heel away from the postero-medial wall of the ascending aorta. Conversely, one could maintain greater contact between the heel of the catheter 400 and the postero-medial wall but would then sacrifice stable coaxial intubation. Accordingly, the Arani catheter 400 cannot simultaneously achieve the optimal combination of coaxial intubation of the tip and superior backup support desirably achieved by direct and stable contact of a heel of a catheter with the postero-medial wall 516.

This failure to achieve this optimal combination results from the inefficient configuration of the single straight tip portion 410. As the tip is further intubated into the ostium 520, the straightness and relative rigidity of tip portion 410 prevents the catheter 400 from adapting to achieve substantial and stable contact between any significant portion of the catheter 400 (usually the heel of the catheter) and the wall of the ascending aorta 512. The straightness of tip portion 410 "pulls" the heel of the catheter 400 downward to hang suspended in the ascending aorta, as opposed to the straight tip portion 410 having some curvature and the ability to flex in order to maintain backup support from the heel of the catheter during further intubation of the tip.

The straightness of straight tip portion 410 and the acute primary curve portion 408 also makes the Arani-type catheter 400 undesirable to use because they make the catheter 400 generally inconvenient to intubate the right main coronary artery 518. Because of the length and straightness of portion 410 and the 90° (or 75°) sharp angle of the primary curve portion 408, these portions of the catheter 400 frequently do not permit quick and easy upward or downward movement (or minimal rotation) of the tip 412 without some "lurching" of the catheter 400, i.e., the catheter catching the wall of the ascending aorta 512 during such up or down movement and then releasing forcefully because of the stored energy from "catching" the wall. This occurs because the tip portion 410 is generally designed to equal or slightly exceed the width of the ascending aorta 512 such that the tip 412 may easily lodge into the ascending aortic wall causing the primary curve to buckle and store energy as the catheter is further advanced. This is just one of the many problems that make the Arani catheter hard to manipulate.

As seen in FIG. 2C, the buttressed position is achieved by distally advancing the Arani catheter 400 so that the secondary curve 404 of the catheter 400 contacts the antero-lateral wall 514 of the ascending aorta 512. As the catheter 400 is advanced to this position, the primary curve 408 of the catheter drops lower into the ascending aorta to be positioned within the Sinus of Valsalva 526 below the ostium 524 of the left coronary artery 522. In this buttressed position, the straight portion 406 proximal of primary curve 408 of the catheter barely contacts the postero-medial wall 516 of the ascending aorta 512 and the primary curve 408 hangs suspended within the ascending aorta 512. Any stenotic push back forces placed on the guide catheter are, in the first instance, directed downward toward the aortic valve through the straight portion instead of being directed across the ascending aorta to the postero-medial wall 516. Of course, this results in a lack of direct stable backup support for the catheter 400 in the ascending aorta 512 directly across from the right main coronary artery 518, where support is needed most.

This "dropping" of the primary curve 408 within the ascending aorta 512 also may result in the tip 412 disengaging from the ostium 520 because the straight portion 410 cannot traverse the distance from the postero-medial wall of the Sinus of Valsalva 526 to the ostium 520. Moving the catheter to a buttressed position effectively reduces the effective length of the tip 412 because at least a portion of the straight portion 410 of the tip 412 is forced at an angle upward through the ascending aorta 512 as the primary curve 408 "drops". The Arani-type catheter 400 is generally designed with a tip 412 and straight portion 410 length sufficient to extend across the ascending aorta 512 (when in the fulcrum position) and to be capable of marginally coaxially intubating a horizontal take-off right coronary artery 518. When moved to the buttressed position, this tip 412 and straight portion 410 length are no longer adequate to extend from the postero-medial wall 516 of the ascending aorta 512 to the ostium 520 and still maintain secure and coaxial intubation of the tip 412 of the catheter 400. Consequently, if the physician chooses to maintain coaxial intubation of the tip, direct backup support will be sacrificed. Conversely, if more backup support is desired, attempts to use the buttress position will make it more likely that the tip 412 will become disengaged from the ostium 520. Accordingly, the Arani-type catheter 400 when used in the buttressed position has several problems: a lack of direct backup support, inadequate tip length, and potential angled tip entry into the ostial wall. In addition, two other significant problems with the Arani catheter as used in the buttress position results from the very sharp acute angles that are created in the body of the catheter 400 (even sharper than the already sharp 75° or 90° primary curve and 90° secondary curve in a relaxed state). First, such acute angles greatly dissipate transmission of pushing forces for a therapeutic device extending through the catheter 400 in that position and, in the case of an acute primary curve, pushing on the catheter may cause the curve to close up or become even more acute. These factors both act to significantly limit the ability of a therapeutic device to cross a tight stenosis. Second, any rotation of the catheter 400 initiated at the proximal end gets distorted and dissipated by the sharp bends in the body of the catheter 400. These sharp angles, the contact of the secondary curve portion with the antero-lateral wall, and the absence of other curves in the catheter make it extremely difficult to further manipulate the tip 412 into and around the ostium 520 of the right main coronary artery 518 (to the extent that inadequate tip length problems can be overcome). Moreover, when in the buttressed position with the primary curve angle more acute, even if it engaged an opposite portion of the ascending aorta, the apex of the primary curve would approximate a singular point, thus not providing sufficient area for stable contact with the wall of the aorta. Accordingly, once in the buttressed position, the operator loses almost all control over the ability to position the tip of the catheter 400 and transmission of pushing forces become greatly limited. This loss of tip control can be important for reasserting intubation when the tip is too short, which is a typical problem for the Arani catheter when used in the buttressed position.

However, the problem of inadequate tip length for the catheter 400 when used in the buttressed position cannot be effectively overcome by merely lengthening straight portion 410. If this is done, then it is much more difficult to initiate intubation of the ostium 520 when initially advancing the tip 412 of the catheter 400 into the ascending aorta 512. In this instance, the straight portion 410 generally would be longer than the width of the ascending aorta, and this geometrical relationship would make it extremely difficult to initially advance the catheter 400 so that the tip straight portion 410 becomes sufficiently horizontal to enter the right coronary ostium 520.

With the catheter 400 in the preferred buttressed position (FIG. 2C), the relatively small size of the contact portion and its location substantially above (not directly across from) the ostium 520 of the right coronary artery 518 along the antero-lateral wall 514 directly contribute to the relatively poor backup support of the Arani guide catheter 400 when advancing a therapeutic device adjacent a tight stenosis. First, because the surface area of contact between the secondary curve portion 404 and the aortic wall is so small, the guide catheter 400 is unstable and therefore easier to dislodge from its position against the aortic wall when resistive "pushback" forces are encountered during advancement of a balloon catheter across a stenosis. Moreover, the straight portion 406 of the Arani-type guide catheter 400 (distal of the secondary curve 404 and proximal of the primary curve 408) extends through the ascending aorta 512, barely contacting, if at all, the postero-medial wall 516 of the ascending aorta 512. This lack of contact allows the stenotic "pushback" forces to more easily overcome the friction of the small contact area between the Arani guide catheter and the aortic wall and dislodge the Arani guide catheter from the desired orientation in the aortic complex.

Another significant problem with the Arani guide catheter, or other conventional guide catheters having 90° angles and or acute angles (less than 90°) along their bodies is that it may be difficult to pass some therapeutic devices (such as, e.g., stents, laser catheters, atherectomy catheters) through such sharp angles in a guide catheter. Gradual curves are required to guide these larger devices because of their increased diameter and/or attendant bulky rigid portions.

SUMMARY OF THE INVENTION

The present invention relates to a guiding catheter which is specifically designed to facilitate the maneuvering of a therapeutic device into a selected coronary artery, preferably the right main coronary artery. The present invention recognizes that the problem of backup support must be solved by making a fundamental change in the overall shape/configuration of guiding catheters used for right main coronary arteries.

The uniqueness of the guide catheter of the present invention results from having analyzed the factors that determine optimal support of a guide catheter within an aortic root complex and arranging these factors in a way to maximize backup support for distal advancement of a therapeutic device through the guide catheter of the present invention while maintaining a desired orientation of the distal end of the guide catheter in the ostium of the right main coronary artery. The factors determining the support provided by the guide catheter include the following. First, the invention can attain deep coaxial intubation of a distal tip of the guide catheter within the ostium of the right main coronary artery. Second, the catheter has a smoothness (i.e., lack of steep bends or acute angles) throughout its length when deployed in the cardiovascular system. Third, the catheter achieves a point of backup support against the wall of the ascending aorta that is as close as possible to directly across from the ostium of the right main coronary artery. Fourth, a large supportive segment of the guide catheter can rest against the wall of the ascending aorta to increase stability of the guide catheter within the aortic complex. Fifth, the catheter is capable of providing a substantially linear axis of support between the ostium of the right main coronary artery and the point of support against the wall of the ascending aorta. Sixth, the catheter is able to compensate for anatomical variations such as a Sheperds Crook take off, "anterior take-offs" (including a rotated aortic root or an offset origin of the right coronary artery), or an "exit bend" of the ascending aorta (a pronounced medial curvature of the lower region of the ascending aorta).

Providing a configuration for a guide catheter, such as the present invention, which focuses on combining all of these factors to provide an optimal guide catheter design results in a guide catheter that functions appreciatively better than the Judkins guide catheter, the Arani Double Loop catheter, or any of the known catheters used for angioplasty catheterization of the right main coronary artery.

The guide catheter of the present invention in a relaxed (preformed) state prior to insertion within the cardiovascular system has a configuration that causes the advantageous orientation of the guide catheter in the aortic complex. The inventive guide catheter includes a hollow, flexible tubular body having a proximal, generally straight portion and a distal, generally curvaceous portion with a distal end. The distal portion has a primary curve proximal the distal end, a secondary curve proximal the primary curve, and a tertiary curve proximal the secondary curve. These curves are preformed and aligned so that after the guide catheter has been advanced through the descending aorta, over the aortic arch, and into the ascending aorta to a position where the distal end is generally coaxially aligned relative to the ostium of the right main coronary artery, the distal portion of the guide catheter engages the wall of the ascending aorta and engages the wall of the aortic arch.

Preferably, the proximal and secondary curves are defined by preformed, consecutively arranged obtuse angled segments of the tubular body. The tertiary curve is defined by a preformed, oppositely disposed arc extent of the tubular body long enough to cause the distal portion to overlie itself in its preformed configuration prior to use.

The advantageous orientation of the guide catheter of the present invention (when in the aortic complex) results directly from the configuration of the guide catheter when in its relaxed (preformed) state prior to insertion in the cardiovascular system. Foremost, one embodiment of the guide catheters of the present invention has an "over-curved" tertiary curve portion including a supportive fifth curved segment positioned proximally of the secondary curve portion (and the primary curve). The tertiary curve portion forms an arc of between 260° to 330°. This tertiary curve portion causes the supportive fifth curved segment and a proximal portion of the secondary curve portion to form the contact portion (in use) that rests substantially contiguous against the wall of the ascending aorta. This arrangement causes at least a portion of a supportive fifth curved segment to press against the ascending aortic wall, thereby allowing the primary point of backup support (at a distal end of the area of support, i.e., a distal end of the contact portion) to be positioned very low in the ascending aorta. The preferred initial point of backup support for the guide catheter of the present invention is a point along the ascending aortic wall substantially directly opposite the ostium of the right main coronary artery. Moreover, because the supportive fifth curved segment of the guide catheter of the present invention presses against the ascending aortic wall, a large area of general backup support (the substantially contiguous contact portion) is provided for the guide catheter which aids in the backup process by making it quite difficult to dislodge the guide catheter from its desired orientation.

In addition, the presence of the tertiary curve portion (which is preferable defined by a series of relatively gradual bends) provides a single longer bent section of the guide catheter (than a Judkins-style or an Arani-style guide catheter) when disposed in the aortic complex. Each bend in the tertiary portion of the catheter has a relatively mild angle to allow a fuller transmission of distal pushing forces through the guide catheter. This arrangement thus facilitates the passage of therapeutic devices through the inventive guide catheter, especially when such devices have rigid and/or bulky portions, as the case may be for a stent or arthrectomy catheter.

All of these advantages of the guide catheter of the present invention are gained by an intentional design for the configuration of the guide catheter in its relaxed state. Accordingly, when the guide catheter of the present invention is fully disposed in the aortic complex, a substantially different and superior (i.e., better) orientation is achieved, compared to previous catheters.

BRIEF DESCRIPTION OF THE DRAWINGS

The above brief description, as well as further objects, features and advantages of the present invention will be more fully appreciated by reference to the following detailed description of the presently preferred but nonetheless illustrative embodiments in accordance with the present invention when taken in conjunction with the accompanying drawings wherein:

FIGS. 1A and 1B are side and front views, respectively, of a portion of the Judkins-type catheter of the prior art;

FIGS. 3A–3D, 4A–4D, 5A–5D, 6A–6D and 7A–7D are views similar to FIGS. 1A–1D, respectively, but depicting alternate embodiments of the present invention;

FIGS. 8A and 8B are side views of a portion of the another embodiment of the catheter of the present invention;

FIG. 8C is a top view of a modified version of the catheter of FIGS. 8A and 8B, as viewed from the top of FIGS. 8A and 8B;

FIGS. 10A and 10B are side views of a portion of the another embodiment of the catheter of the present invention;

Figure 1C:
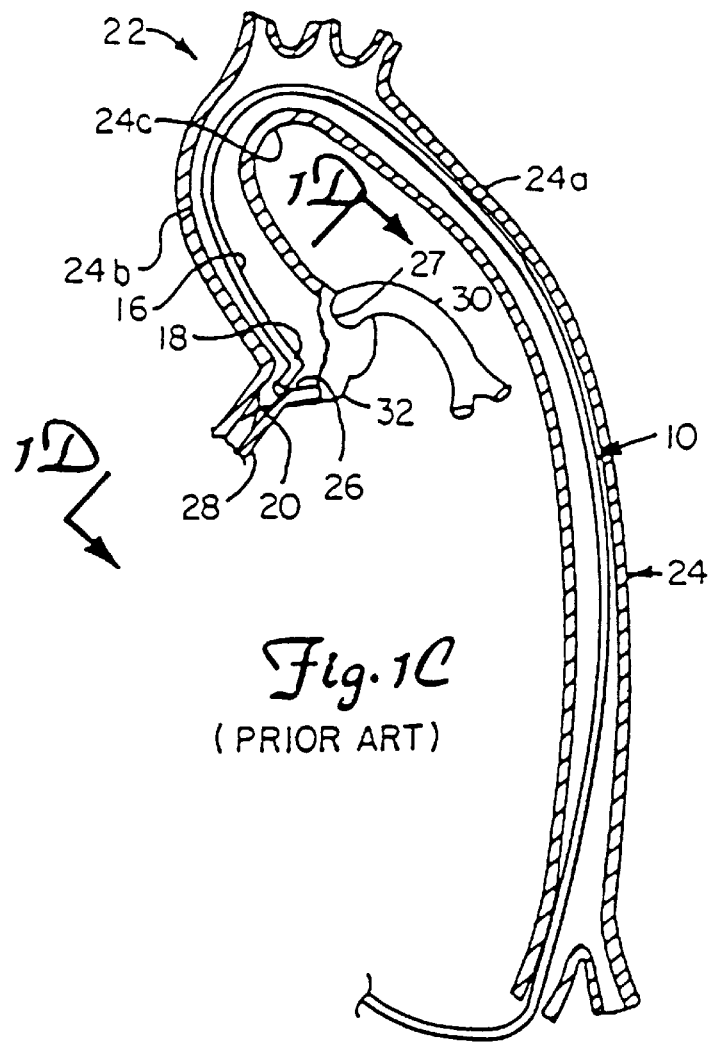
FIG. 1C is a cross sectional view of a portion of a cardiovascular system with the catheter of FIGS. 1A and 1B inserted therein.
Figure 1D:
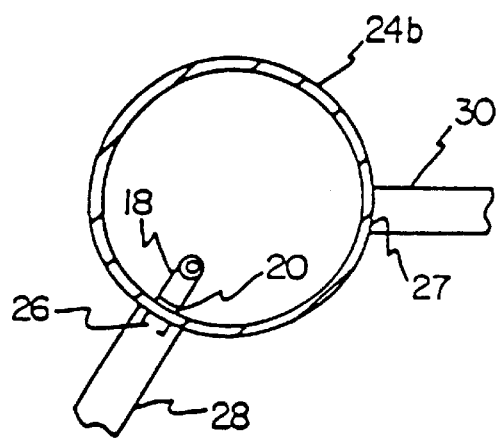
FIG. 1D is an enlarged cross-sectional view taken along the line 1D—1D.

While the above identified drawings set forth several preferred embodiments, other embodiments of the present invention are also contemplated, as noted in the discussion. This disclosure presents illustrative embodiments of the present invention by way of representation and not limitation. It should be understood that numerous other modifications and embodiments can be devised by those skilled in the art which fall within the scope and spirit of the principles of this invention.

DETAILED DESCRIPTION OF THE PREFERRED EMBODIMENTS

One embodiment of the catheter of the present invention is shown in general by the reference numeral 36 in FIGS. 3A–3D. The catheter 36 is in the form of an elongated, preformed tubular member having a straight portion 38 extending from the proximal end portion (not shown) of the catheter 36. The catheter 36 includes a distal end portion formed by a curved portion 40, a plurality of straight portions 42, 44, and 46, and a tip portion 48. The curved portion 40 extends from the straight portion 38 for approximately 200–240°. The straight portion 42 extends from the curved portion 40 toward, and at an angle to, the straight portion 38. The straight portion 44 extends from, and at an angle to, the straight portion 42, and generally parallel to the straight portion 38. The straight portion 46 extends from, and at an angle to, the straight portion 44 and the tip portion 48 extends from, and at an angle to, the straight portion 46 and generally perpendicular to the straight portion 38.

The curved portion 40 has a radius of curvature of approximately 5 cm. and the distance D1 between the tip portion 48 and the outer edge of the curved portion 40 is approximately 12.5 cm. The distance D2 between the straight portions 44 and 38 is approximately 2.5 cm. The straight portion 44 is approximately 1.5 cm. in length, and the straight portions 46 and 48 are each approximately 1.2 cm. in length. The angle between the straight portions 42 and 44 is between 20° and 50°, the angle between the straight portions 44 and 46 is between 10° and 50°, and the angle between the straight portion 46 and the tip portion 48 is between 10° and 50°. It is understood that these distances and angles represent only one possible configuration of the catheter 36. For example, the length of straight portion 44 can be increased to other values within the scope of the invention and thus provide increased support as compared to the Judkins catheter.

The aforementioned dimensions can vary substantially and depend extensively on the variance of human cardiovascular physiology. For example, while the curved portion 40 typically will have a radius of curvature of approximately 5 cm., the radius of curvature can vary from approximately 5 to 7 cm. Similarly, the distance D1 can vary from approximately 6 to 16 cm., the distance D2 can vary from approximately 0.0 to 6 cm., and the straight portions 46 and 48 can vary from 0.5 to 2 cm. in length.

Figure 3A:
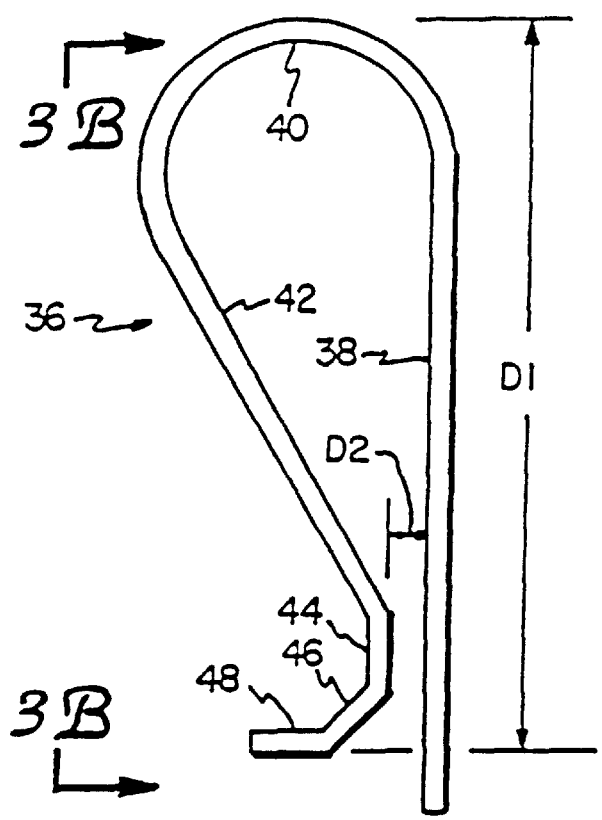
Figure 3B:
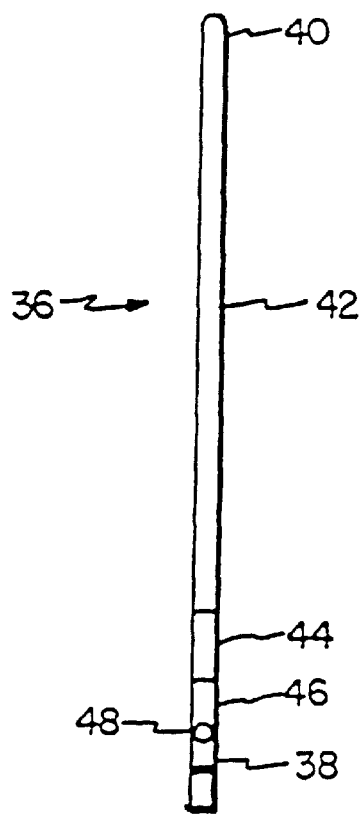

Referring to FIG. 3B, it is noted that the straight portion 38 extends in the same plane as the above described distal end portion.

The catheter 36 can be fabricated of a material, such as plastic, which exhibits optimum flexibility and softness while permitting the transmission of twisting forces along its length by manipulation of its proximal end. The material is tubular, i.e. it has a continuous bore extending through its entire length for receiving other catheters, wires or the like as discussed above. Since this material is conventional it will not be described in any further detail.

Figure 3C:
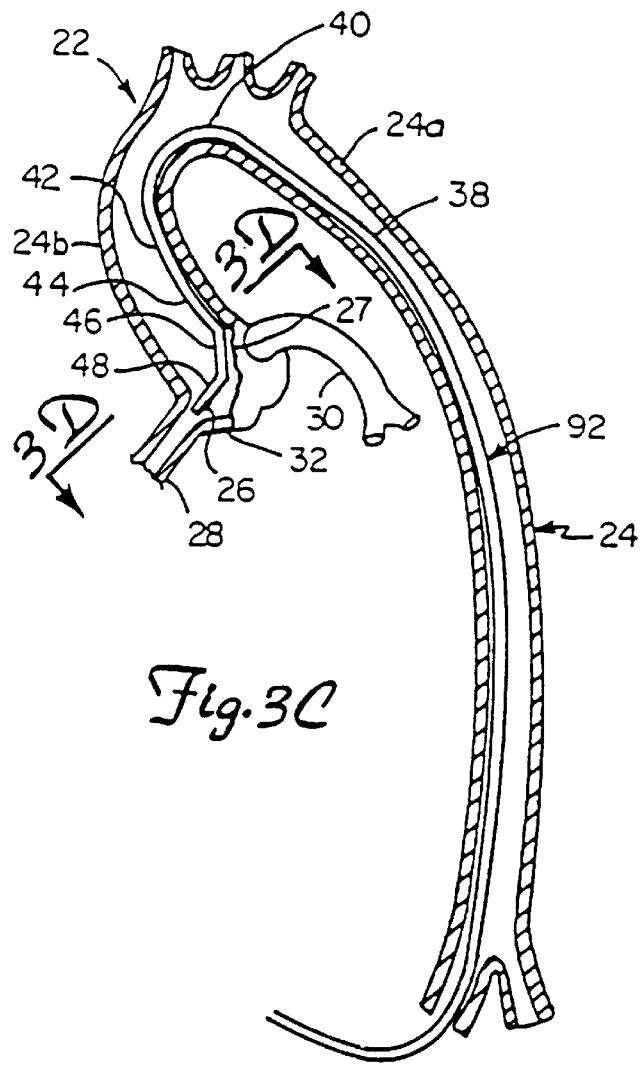
Figure 3D:
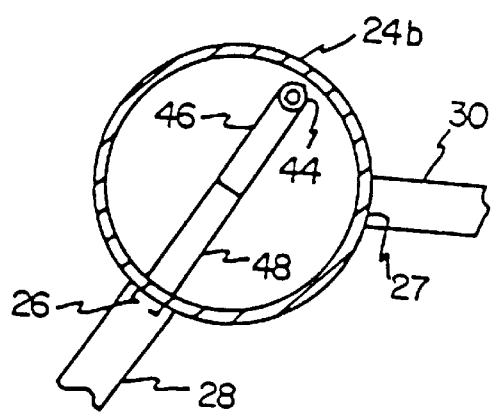

FIGS. 3C and 3D depict the cardiovascular system 22 of FIG. 1C with the catheter 36 inserted therein. Prior to insertion, a relatively stiff wire (not shown) is inserted in the catheter 36. After the catheter 36 is inserted in the system 22, the wire is withdrawn and the catheter 36, by virtue of its preformed shape previously described and shown in FIGS. 3A and 3B, takes the position shown in FIGS. 3C and 3D, or with slight manipulation, with the tip portion 48 precisely aligned with the ostium 26 of the right coronary artery 28 in a coaxial relationship. It is also noted that, as a result of the foregoing, a substantial portion of the catheter 36 will usually rest against the inner wall of the aorta 24, including the descending aorta 24a, the aortic arch 24c and the ascending aorta 24b, and bends at a lesser angle compared to the Judkins catheter 10. Also, the straight portion 44 rests against the wall of the ascending aorta 24b opposite the ostium 26 of the right coronary artery 28. Thus, the catheter 36 is supported by the wall when axial forces are exerted on the tip portion 48 and the tip portion 48 remains fixed in the lumen of the right coronary artery 28.

Referring to FIGS. 4A–4D, there is shown an alternate embodiment of the catheter of the present invention. The catheter depicted is shown in general by the reference numeral 50 and is for a special application referred to as 1, anterior take-off 11 of the right coronary artery as will be described.

The catheter 50 is in the form of an elongated, preshaped tubular member having a straight portion 52 extending from the proximal end portion (not shown) of the catheter 50. The catheter 50 further includes a distal end portion formed by a curved portion 54, a plurality of straight portions 56, 58, and 60, and a tip portion 62. The curved portion 54 extends from the straight portion 52 for approximately 200–240°. The straight portion 56 extends from the curved portion 54 toward, and at an angle to, the straight portion 52. The straight portion 58 extends from, and at an angle to, the straight portion 56, and generally parallel to the straight portion 52. The straight portion 60 extends from, and at an angle to, the straight portion 58, and the tip portion 62 extends from, and at an angle to, the straight portion 60 generally perpendicular to the straight portion 52.

Figure 4A:
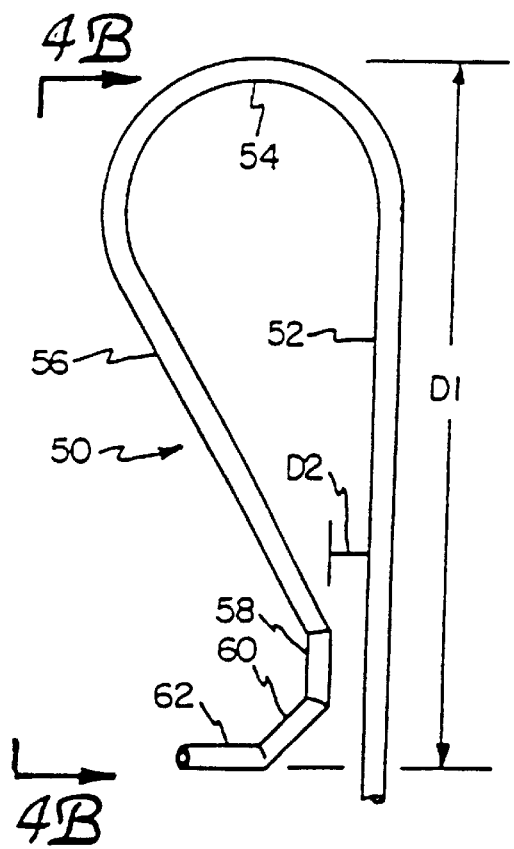
Figure 4B:
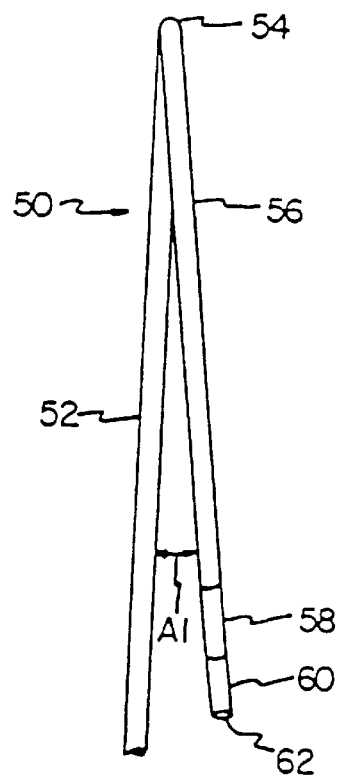
Figure 4C:
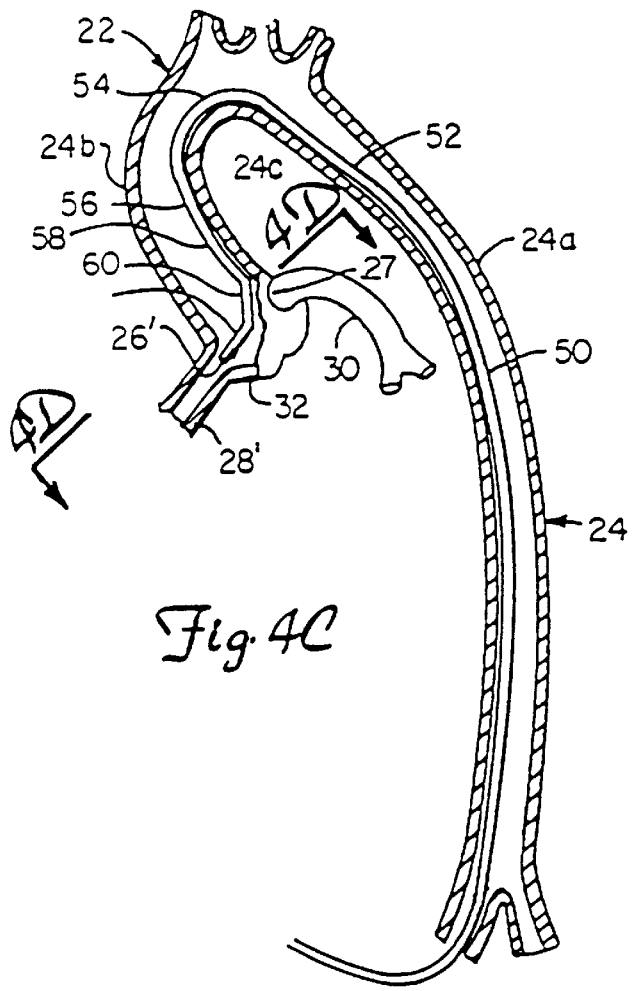

According to a feature of this embodiment, the straight portion 56, and therefore the portions 58, 60 and 62 extending therefrom, are bent out of the plane formed by the straight portion 52 and the curved portion 54 as shown in FIG. 4B. As a result, the straight portion 56 extends at an angle A1 of between 8° to 40° to the straight portion 52. Consequently, the tip portion 62 is displaced from the corresponding portion of the straight portion 52 by approximately 2 cm.

Figure 4D:
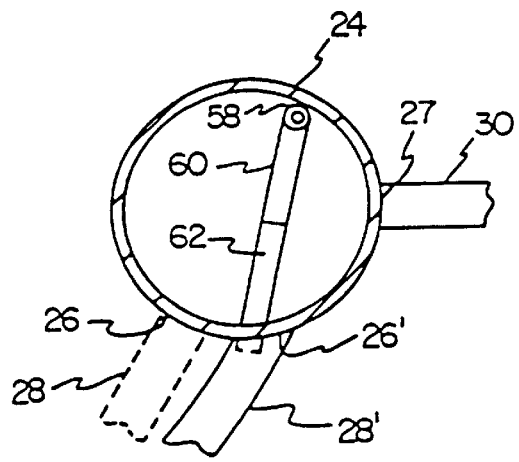
Figure 5C:
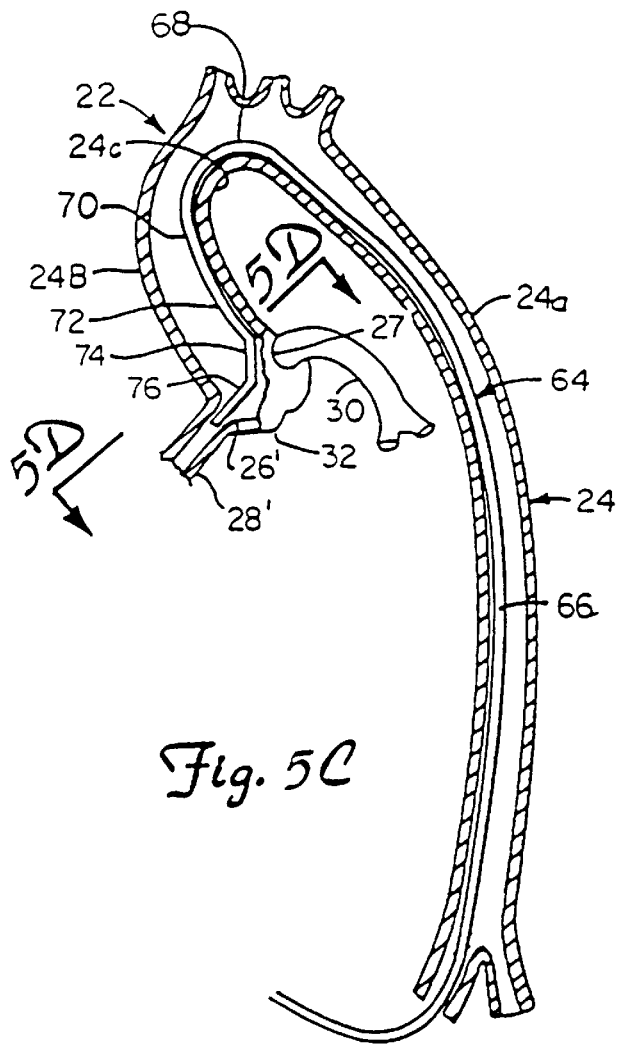
Figure 5D:
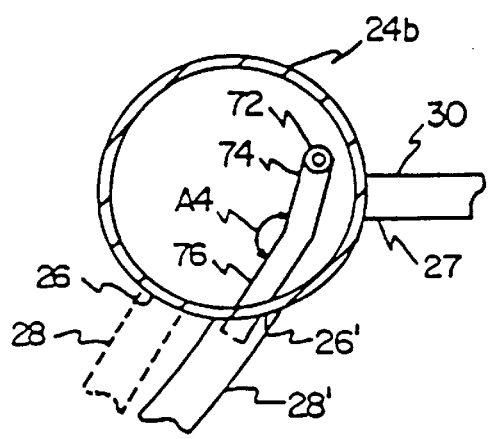
Figure 6C:
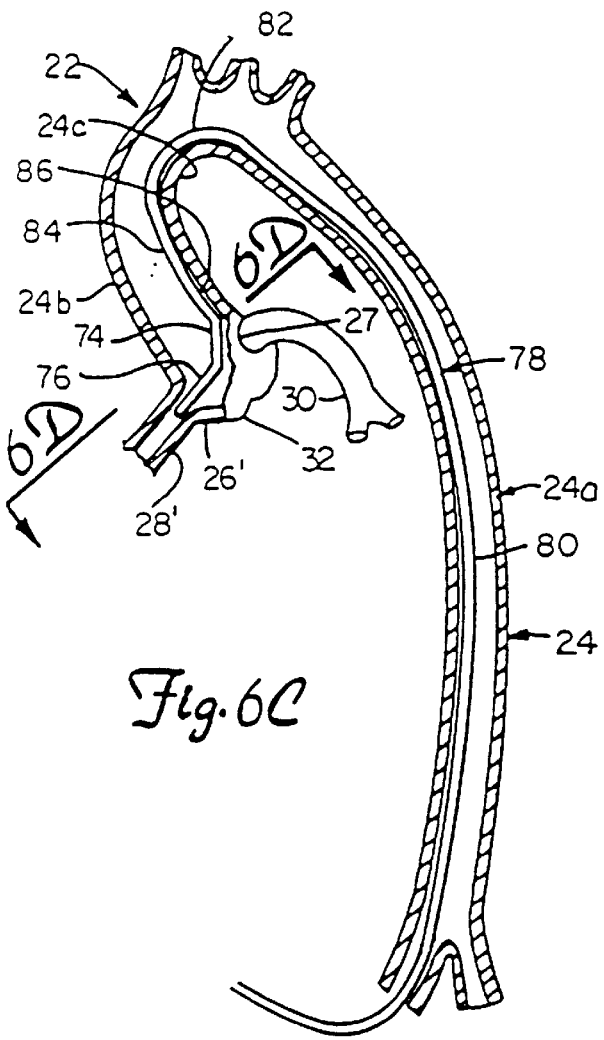
Figure 6D:
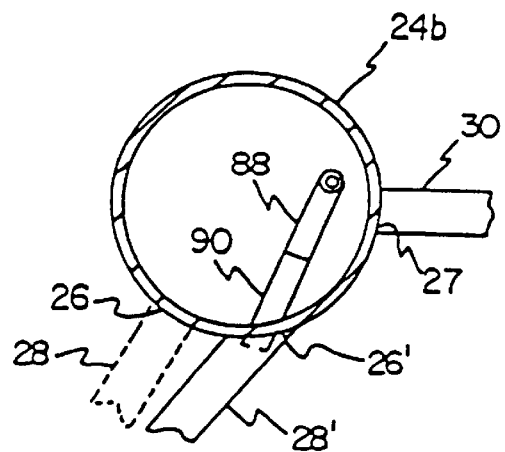
Figure 7C:
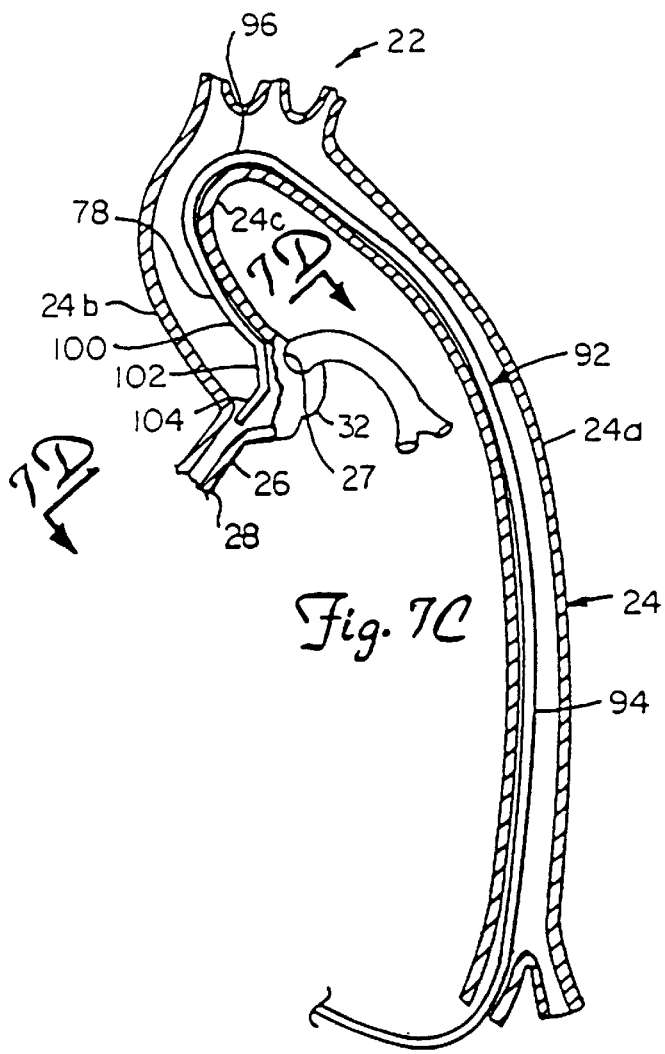
Figure 7D:
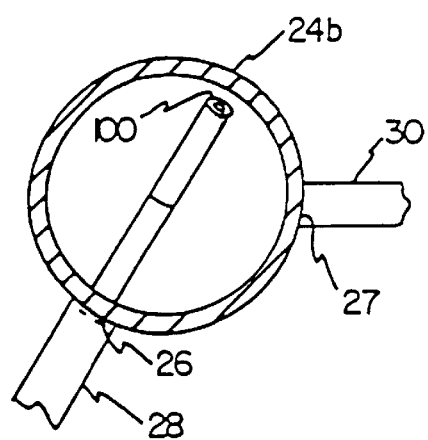

The catheter 50 has a special application in a coronary condition referred to as "anterior take-off" (as seen in RAO view) of the right coronary artery in which the right coronary artery 28 of the cardiovascular system 22 is angularly displaced anteriorly from its normal location, as shown in FIG. 4D. More particularly, the normal position of the right coronary artery is shown by the dashed lines and by the reference numeral 28. However, the right coronary artery sometimes is angularly displaced anteriorly from its normal position to a position shown, for example, by the solid lines and by the reference numeral 28'. Anterior displacements of the right coronary artery 28 may be due to either a displacement in the aortic root or a displacement in the right coronary artery. Both of these variations result in an anterior take-off of the right coronary artery. The catheter 50 is especially configured for this location and, when inserted into the cardiovascular system 22 in the manner described above, takes the position shown in FIG. 4C with the tip portion 62 coaxially aligned with the ostium 26' of the right coronary artery 28'. Thus the catheter 50 enjoys the advantages of the catheter 36 of the embodiment of FIGS. 3A–3D notwithstanding the anterior displacement of the artery.

Referring to FIGS. 5A–5D, there is shown another alternate embodiment of the catheter of the present invention. The catheter depicted is shown in general by the reference numeral 64 and is again for the special application referred to as anterior take-off of the right coronary artery as previously described.

The catheter 64 is in the form of an elongated, preshaped tubular member having a straight portion 66 extending from the proximal end portion (not shown) of the catheter 64. The catheter 64 further includes a distal end portion formed by a curved portion 68, a plurality of straight portions 70, 72, and 74, and a tip portion 76. The curved portion 68 extends from the straight portion 66 for approximately 200–240°. The straight portion 70 extends from the curved portion 68 toward, and at an angle to, the straight portion 66. The straight portion 72 extends from, and at an angle to, the straight portion 70 generally parallel to the straight portion 66. Similarly, the straight portion 74 extends from, and at an angle to, the straight portion 72, and the tip portion 76 extends from, and at an angle to, the straight portion 74 generally perpendicular to the straight portion 66.

As better shown in FIG. 53, the straight portion 72 is bent out of the plane formed by the straight portion 70, the curved portion 68 and the straight portion 66, and extends at an angle A2 of approximately 40° to the straight portion 70. Further, the straight portion 74 is bent back toward the aforementioned plane and extends at an angle A3 of approximately 40° to the straight portion 72. Also, the straight portion 76 is bent back toward the aforementioned plane and extends at an angle A4 (FIG. 5D) of approximately 160° to the straight portion 74.

The catheter 64 has a special application in connection with the anterior take-off of the right coronary artery, as previously described. The catheter 64 is especially configured for this condition and, when inserted into the cardiovascular system 22 in the manner described above, it takes the position shown in FIG. 5C with the tip portion 76 coaxially aligned with the ostium 26' of the right coronary artery 28'. Thus the catheter 64 enjoys the advantages of the catheter 36 of the embodiment of FIGS. 3A–3D notwithstanding the anterior displacement of the right coronary artery.

Referring to FIGS. 6A–6D, there is shown another alternate embodiment of the catheter of the present invention. The catheter depicted is shown in general by the reference numeral 78 and is also for anterior take-off of the right coronary artery as previously described.

The catheter 78 is in the form of an elongated, preformed tubular member having a straight portion 80 extending from the proximal end portion (not shown) of the catheter 78. The catheter 78 further includes a distal end portion formed by a curved portion 82, a plurality of straight portions 84, 86, and 88, and a tip portion 90. The curved portion 82 extends from the straight portion 80 for approximately 200–240°, and the straight portion 84 extends from the curved portion 82 toward, and at an angle to, the straight portion 80. The straight portion 86 extends from, and at an angle to, the straight portion 84 generally parallel to the straight portion 80. Similarly, the straight portion 88 extends from, and at an angle to, the straight portion 86, and the tip portion 90 extends from, and at an angle to, the straight portion 88.

The embodiment of FIGS. 6A–6D enjoys the same planar relationships, as the embodiment of FIGS. 3A–3D with two additional features. As better shown in FIG. 6B, the straight portion 84 is bent out of the plane formed by the straight portion 80 and the curved portion 82 and extends at an angle A4 of approximately 10–30° to the straight portion 80. Also, the straight portion 86 is bent at an angle A5 of approximately 0–30° to the straight portion 84 in the opposite direction of A4, i.e. back towards the straight portion 80. In a preferred embodiment, the angle A4 is 20° and the angle A5 is 30°.

The catheter 78 has a special application in connection with the anterior take-off of the right coronary artery, as previously described. When inserted into the cardiovascular system 22 in the manner described above, the catheter 78 takes the positions shown in FIGS. 6C–6D with the tip portion 90 coaxially aligned with the ostium 26' of the right coronary artery 28'. Thus the catheter 78 enjoys the advantages of the catheter 36 of the embodiment of FIGS. 3A–3D notwithstanding the anterior displacement of the artery.

Referring to FIGS. 7A–7D, there is shown still another alternate embodiment of the catheter of the present invention which is referred to in general by the reference numeral 92. This alternate embodiment can be designed for use either with a standard anatomy or when there is an anterior take-off of the right coronary artery, as previously described.

The catheter 92 is in the form of an elongated, preformed tubular member having a straight portion 94 extending from the proximal end portion (not shown) of the catheter 92. The catheter 92 further includes a distal end portion formed by a curved portion 96, a plurality of straight portions 98, 100, and 102, and a tip portion 104. The curved portion 96 is "overcurved" in this embodiment for reasons described below such that it extends from the straight portion 94 for approximately 260–320°. The straight portions 98, 100, and 102, and the tip portion 104 are shaped as their counterparts in the previous embodiment shown in FIGS. 4A–4D. In FIG. 7B, these portions are shown as being out of the plane formed by the straight portion 94 and the curved portion 96, however, they are not preformed to be out of the aforementioned plane, but are necessarily so due to the extended curvature of the curved portion 96.

The curved portion 96 of the catheter 92 is "overcurved" to alleviate two common problems. First, the extended curvature is necessary to compensate for the extra flexibility imparted to catheters as they warm to body temperature. If the curved portion 96 was not "overcurved," then as the catheter 92 warmed and became more flexible, the curved portion 96 would open and enlarge to an angle greater then the angle of the aortic arch 24c. Second, the extended curvature is necessary for support when the aortic arch 24c, which normally curves over 180°, is curved to a greater extent. In both cases, the result is a catheter 92 which no longer rests against the inner wall of the aorta 24, thereby forfeiting the support afforded when the straight portion 100 rests against the ascending aorta 24b wall opposite the ostium 26 of the right coronary artery 28. By "over curving" the curved portion 96, the catheter 92 will rest against the inner wall of the aorta 24 (see FIG. 7C) and provide the needed support.

While the embodiment shown in FIGS. 7A–7D is for standard anatomy, it is also applicable for those earlier embodiments described for use when the right coronary artery has an anterior take-off in that various portions of the catheter 92 can be bent out of the plane formed by the straight portion 94 and the curved portion 96 to allow the tip portion 104 to align with the lumen of a right coronary artery having an anterior take-off.

Additional embodiments of the guide catheters of the present invention for catheterization of a right main coronary artery provide further illustration of the features of embodiments of the present invention described above. These additional embodiments of the present invention include substantially the same strategically ordered sequence (particularly with respect to the embodiments of FIGS. 7A–7D) of straight portions, curve portions, and tertiary curve portions resulting in more precise coaxial alignment of the guide catheter within the ostium of the right main coronary artery, increased support and guidance for therapeutic devices, and a fuller transmission of pushing forces. The previously described guide catheter embodiment of the present invention for catheterization of a right main coronary artery, e.g., the guide catheter embodiment of FIG. 7A, and these additional embodiments, include a unique overcurved tertiary portion created between an otherwise conventional first straight portion and a secondary curve portion of the guide catheter of the present invention. In the previously described embodiment (e.g., the FIG. 7A embodiment), a straight portion 98 was included between the tertiary curve portion (curve portion 96) and the secondary curve portion (the junction of straight portion 98 and straight portion 100). These additional embodiments include a tertiary curve portion (in FIG. 7A, the curved portion 96) but preferably do not include a straight portion like that of straight portion 98 in embodiment 7A. These additional embodiments also include a mild obtuse angle primary curve portion like that shown in the FIG. 7A embodiment (the junction of the portion 104 and portion 102). These additional embodiments provide further examples illustrating the strategic sequencing of straight, curved, and tertiary portions that yield the many advantages of the guide catheters of the present invention, particularly those used for catheterization of a right main coronary artery.

Figure 8A:
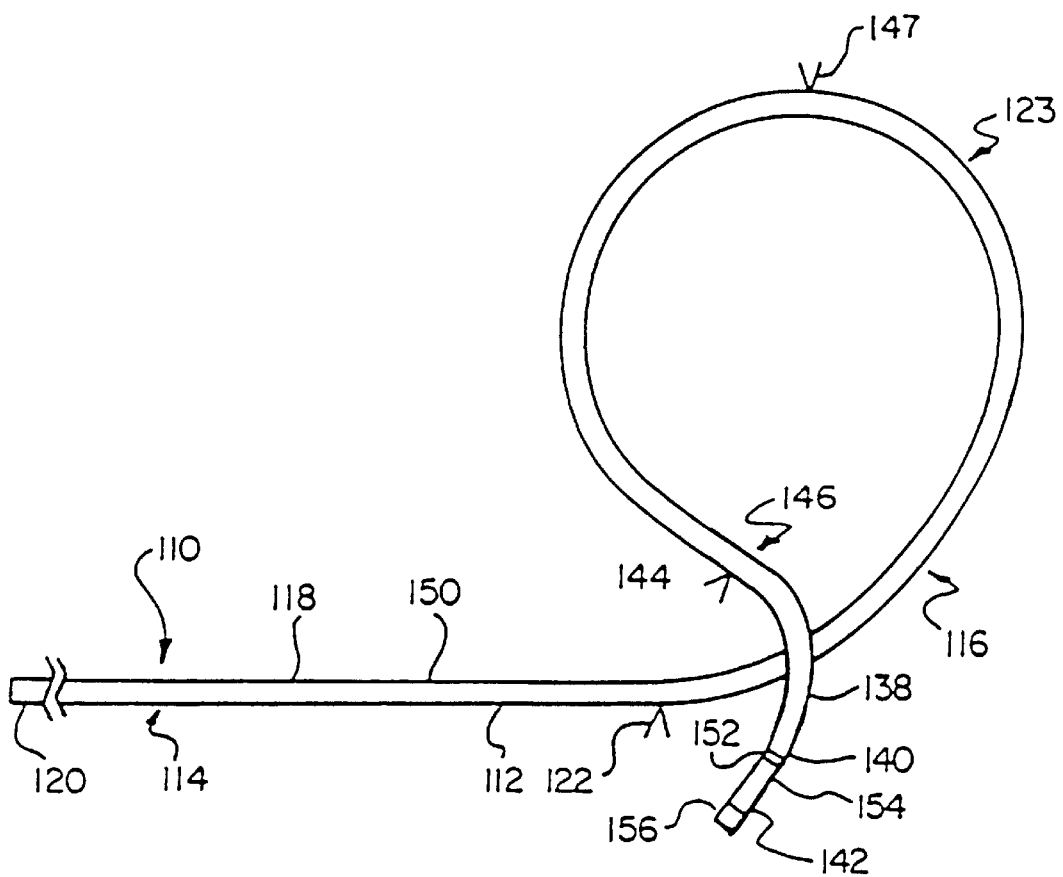

A guide catheter 110, another preferred embodiment of the present invention, is illustrated in FIGS. 8A–8C. The guide catheter 110 is adapted for use with a right main coronary artery to facilitate advancement of a dilatation balloon catheter (or other intravascular devices) through the guide catheter 110. The preformed guide catheter 110 is shown in FIG. 8A in a relaxed or "equilibrium" state prior to insertion into the cardiovascular system and includes a hollow elongate flexible tubular body or shaft 112 which extends from a proximal generally straight portion 114 to a distal generally curvaceous portion 116. The guide catheter 110 includes a first straight proximal portion 118 that extends from a proximal end 120 of the guide catheter 110 to a point 122 (a distal end of the first straight portion 118) located distally along the catheter shaft 112 from the proximal end 120. A fitting or manifold (not shown) is typically mounted on the proximal end of a guide catheter.

The first straight portion 118 preferably has a length of about 90 to 95 centimeters but can be made shorter or longer to accommodate different patient anatomies. The distal portion 116 of the guide catheter 110 includes consecutively arranged portions including a tertiary curved portion 123, a secondary curved portion 146, and a distal tip portion further including a second straight portion 138, a primary curved portion 140, and a straight tip portion 142. The tertiary curve portion 123 forms an arc that curves oppositely from the obtuse angles created by the primary and secondary curve portions, 140 and 146, respectively, and is long enough to cause the distal portion 116 of the guide catheter 110 to overlie itself in its relaxed, preformed configuration prior to use.

The tertiary curve portion 123 of the guide catheter 110 is defined by the curvature in the guide catheter 110 between the point 122 and a point 144 (a distal end of the tertiary portion 123) located distally along the catheter shaft 112. As seen in FIG. 8B, the secondary curve portion 146 extends distally from the distal end of the tertiary curve portion 123, from the point 144 to a point 137. The second straight portion 138 extends distally from a distal end of the second curved portion 146, from the point 137 to a point 139. The primary curve portion 140 extends distally from the distal end of the second straight portion 138, from the point 139 to a point 141. The straight tip portion 142 extends distally from the primary curved portion 140, from the point 141 to a point 143 (which defines a terminal distal end of the guide catheter 110).

The tertiary portion 123 of the guide catheter 110 is a curvaceous segment forming an arc from between 260 and 330° and is comprised of the preferred combination of five discrete portions: a first curved segment 124, a second curved segment 126, a third curved segment 128, a fourth curved segment 130, and a fifth curved segment 132. As shown in FIGS. 8A–8B, the tertiary portion 123 forms an arc of about 330°.

The first curved segment 124 of the tertiary curve portion 123 extends distally from the point 122 to a point 125 along the catheter shaft 112. The arc of the first curved segment 124 is about 270, has radius of curvature of about 3.5 centimeters, and is about 1.65 centimeters long. The second curve segment 126 of the tertiary curve portion 123 of the guide catheter 110 is defined by the curvaceous segment of the catheter shaft 112 extending distally from the point 125 to a point 127 along the catheter shaft 112. The second curved segment 126 forms an arc of about 55°, has a radius of curvature of about 5.5 centimeters, and is about 5.3 centimeters long. The third curved segment 128 of the tertiary curved portion 123 extends distally from the point 127 to a point 129 along the catheter shaft 112. The third curved segment 128 forms an arc of about 153°, has a radius of curvature of about 3.0 centimeters, and is about 8.0 centimeters long. The fourth curved segment 130 of the tertiary curved portion 123 extends distally from the point 129 to a point 131 along the catheter shaft 112. The fourth curved segment forms an arc of about 69°, has a radius of curvature of about 2.8 centimeters, and is about 3.4 centimeters long. The fifth curved segment 132 of the tertiary curved portion 123 extends distally from the point 131 to the point 144 along the catheter shaft 112. The fifth curved segment 132 forms an arc of about 25°, has a radius of curvature of about 6.0 centimeters, and is about 2.6 centimeters long.

The secondary curved portion 146 is preferably comprised of two discrete curved segments: a first curved segment 134 and a second curved segment 136. The first curved segment 134 forms an arc of about 20°, has a radius of curvature of about 2.0 centimeters, and is about 0.70 centimeters long. The second distal curved segment 136 forms an arc of about 50°, has a radius of about 1.5 centimeters, and is about 1.3 centimeters long.

The second straight portion 138 of the guide catheter extends about 0.30 centimeters from the distal end of the secondary curved portion 146 from the point 137 to a point 139 along the catheter shaft 112. The primary curved portion 140 extends from the second straight portion 138 from the point 139 to a point 141. The primary curved portion 140 forms an arc of about 25°, has a radius of about 2.0 centimeters, and is about 0.85 centimeters long. The straight tip portion 142 extends distally from the primary curve portion 140 for about 0.95 centimeters. The primary curve portion forms an obtuse angle of approximately 25° between second straight portion 146 and the straight tip portion 142.

The distance D1 (see FIG. 8B) from the point at which the distal portion 116 overlaps itself to a point 147 diametrically opposite therefrom along the tertiary curve portion 123 is about 7.45 centimeters. The distance D2 in FIG. 8B is about 6.0 centimeters. The distance from point 147 to the secondary curve portion 146 is about 8.0 to 9.0 centimeters when the guide catheter 110 is fully disposed in the right coronary artery 518 (as in FIG. 9A). The catheter length from the distal end 143 and an apex of the primary curve portion 140 is about 1.4 centimeters. The catheter length from the apex of the primary curve portion 140 and an apex of the second curved portion 136 is about 1.4 centimeters. The catheter length from the apex of the second curved segment 136 and an apex of the first curved segment 134 is about 1.0 centimeters.

Although the guide catheter 110 can be a single piece of tubing with a uniform degree of flexibility throughout its length, the guide catheter 110 preferably is made of two or three principal tubular segments with each successively distal segment having a greater degree of flexibility. As seen in FIG. 8A, the embodiment of the guide catheter 110 having three principal flexibility segments includes a first flexibility tubular segment 150 extending from the proximal end 120 of guide catheter 110 to a bond member 152 located just distal of the primary curve portion 140 (in the distal portion 116 of the guide catheter 110). A second flexibility tubular segment 154 extends distally from the bond member 152 to a third flexibility tubular tip segment 156. In an alternate embodiment, the bond ring member 152 is located proximal of the primary curve portion 140 of the guide catheter 110. Accordingly, the least flexible segment, segment 150, would extend just proximal of the primary curve portion 140 of the guide catheter 110.

The nature of the three principal segments and their different flexibility are described in co-pending application Ser. No. 07/908,250 INTRAVASCULAR GUIDE CATHETER, which is incorporated by reference herein. In one embodiment, the first segment 150, the second segment 154, and the third segment 156 have a Shore D durometer hardness of about, 63, 40, and 35 respectively. The bond member 152 has a Shore D durometer hardness of about 50, intermediate the hardness of the first segment 150 and the second segment 154.

A double flexibility segment embodiment (not shown) of the guide catheter 100 has two principal segments of flexibility, each with a different degree of flexibility. The double flexibility embodiment has a tip segment (like tip segment 156) with a select degree of flexibility and a main segment (all portions proximal to the tip segment) with a different select degree of flexibility (less flexible than the tip segment). The double flexibility segment embodiment differs from the triple flexibility segment embodiment in that the second flexibility segment 154, having a hardness intermediate that of the first (i.e., main) flexibility segment 150 and the tip segment 156, is absent in the double flexibility segment embodiment. Although it is preferred to have a bond ring member (like member 152) positioned between the main and tip flexibility segments, the double flexibility segment may omit a bond ring member between the main segment and the tip segment. In one embodiment, the main segment of the double flexibility segment embodiment of the guide catheter 110 has a Shore D hardness of 63 (or 67, 70) and the tip segment has a Shore D hardness of 35. The optional bond ring member would have a Shore D hardness (e.g., about 46) intermediate that of the first segment and tip segment. The optional bond ring member would preferably be positioned distal of the primary curve portion 140 of the guide catheter 110.

The catheter shaft 112 of both the double flexibility segment embodiment and the triple flexibility segment embodiment is made of an outer layer and an inner layer. The outer layer is preferably formed of a polyether block amide material, such as PEBAX® available from ATOCHEM, INC. (Glen Rock, N.J.), loaded with a radiopaque compound such as bismuth subcarbonate. The inner layer is a coating of lubricous material such as TEFLON® available from E.I. Du Pont: Nemours & Co. (Wilmington, Del.). The first principal segment 150 and the second (intermediate) segment 154 (in the triple flexibility embodiment) preferably have a reinforcing layer of wire braiding (of stainless steel wire) extending along the catheter shaft 112 between the inner layer and the outer layer. The tubular tip segment 156 is formed from PEBAX material, loaded with a radiopaque compound such as bismuth subcarbonate.

The configuration of the guide catheter 110 is created by fitting the tubing comprising the catheter (without curves) into a mold having the desired curves and straight segments. The catheter tubing is then heat set into that shape by infrared heating and then cooled as is known in the art. This molding technique produces the configuration of the guide catheter 110 as shown in FIGS. 8A–8C, FIGS. 10A–10C, FIGS. 11 and 12, as well as any one of the catheters of the present invention described herein.

The guide catheter 110, in one embodiment, overlies itself as generally depicted by FIG. 8B. FIG. 8C also shows an alternate embodiment of the inventive guide catheter in which a portion of the guide catheter 110A extends in multiple planes to yield a three dimensional type distal portion 116 of a guide catheter 110A. The segments of the guide catheter 110A have the same lengths and curvatures as the guide catheter 110 shown in the view FIG. 8B. However, as seen in this top view of the guide catheter 110A in FIG. 8C, the guide catheter 110A has curves planes in several planes. The guide catheter 110A of FIG. 8C has a proximal first segment 170, a straight second segment 172, a curved third segment 174, a straight fourth segment 176, a curved fifth segment 178, and a sixth distal straight segment 180.

The angle ($\alpha_1$) between the first segment 170 and the second segment 174 is about 22 degrees and the length of the second segment 172 is about 5.35 centimeters. The third segment 174 has a radius of curvature of about 10 centimeters and forms an arc of about 5 degrees. In an alternate embodiment, the third segment 174 can be straight and extend about 1.0 centimeters. The fourth segment 176 has a slightly curved proximal portion extending from the third segment 174 and then has a straight portion extending distally for about 3.0 centimeters. The angle between the plane traversed by the third segment 174 and the plane traversed by the straight portion of the fourth segment 176 is about 60°. As seen from the top view of FIG. 8C, the straight portion of fourth segment 176 forms an obtuse angle ($\alpha_2$) of about 130 degrees relative to the first segment 170 over which the fourth segment 176 crosses. The distance between the crossover of the fourth segment 176 and the junction of the first segment 170 and the second segment 172 is about 4.5 centimeters. The fifth segment 178 has a radius of curvature of about 1.5 centimeters and forms an arc of about 60 degrees. The sixth segment 180 extends from segment 178 and has a length of about 1.0 centimeter. The distance D3 between the crossover of the fourth segment 176 and the first segment 170 to the tip of segment 180 is about 3.0 centimeters. The distance D4 between the apex of the third segment 174 and the first segment 170 is about 2.0 centimeters.

Figure 9A:
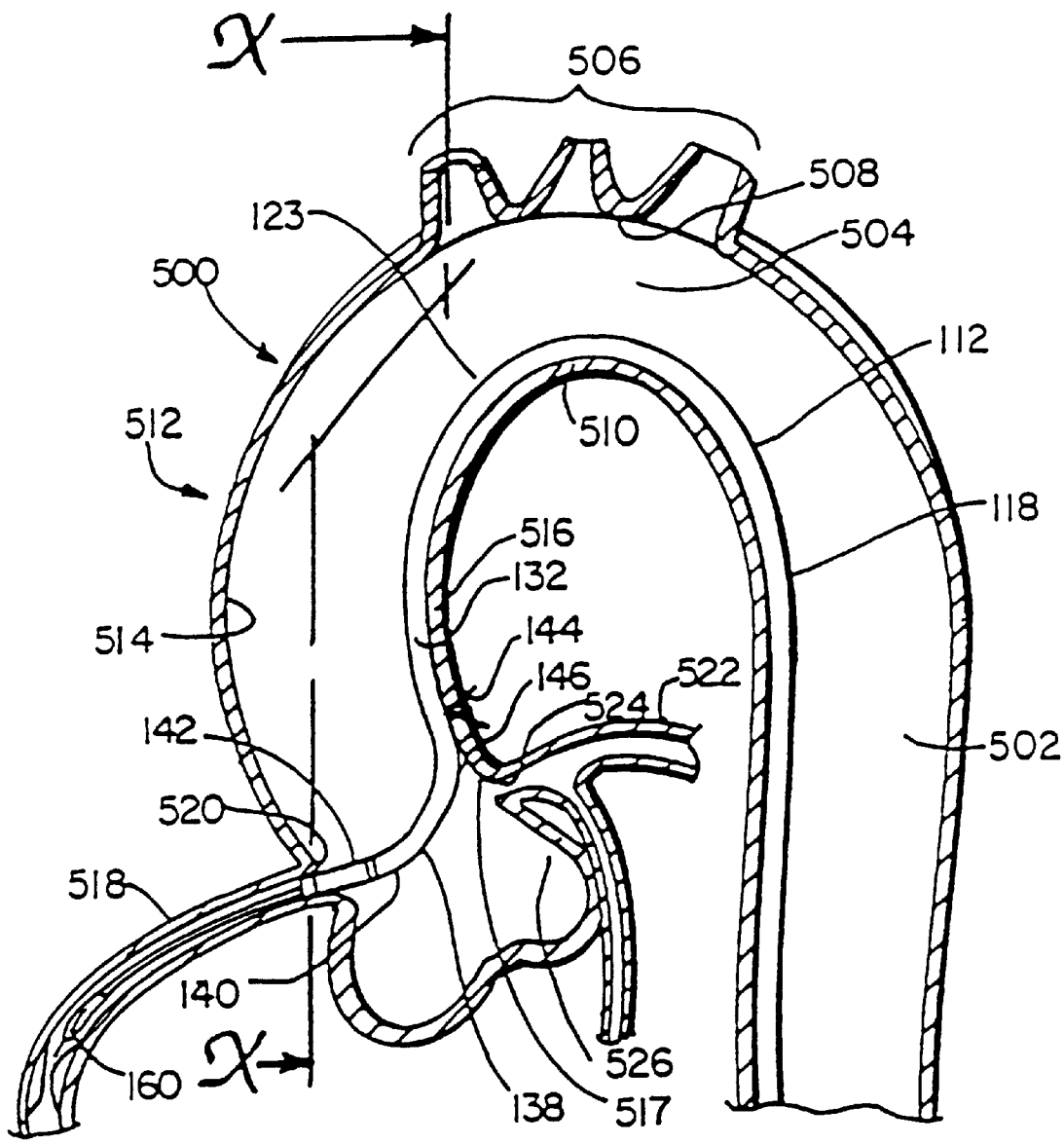
FIGS. 9A, 9B and 9C are cross-sectional views taken from a left anterior oblique view of a portion of a cardiovascular system showing the alternative positions attainable with the inventive catheters of FIGS. 8A, 8B and 8C for intubation of the right main coronary artery.
Figure 9:
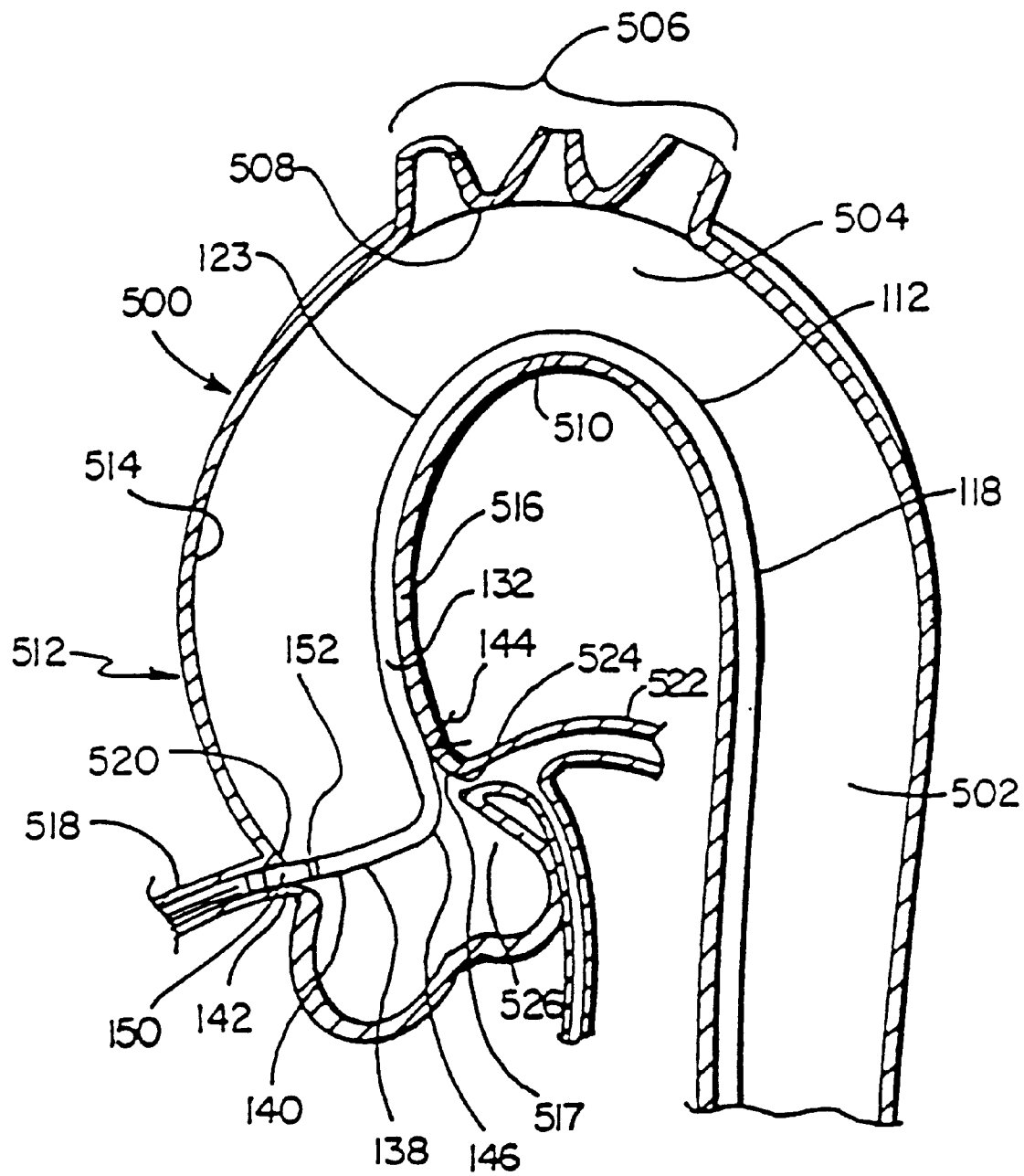
FIG. 9D is a cross-sectional view taken from a left anterior oblique view of a portion of a cardiovascular system having a bent aortic arch and showing one of the alternative positions attainable with the inventive catheters of FIGS. 8A, 8B and 8C for intubation of the right main coronary artery.
FIG. 9E is a generated view in section taken from an anterior posterior view as taken along lines X—X in FIG. 9A.
FIG. 9F is a generated view in section taken from an anterior posterior view as taken along lines Y—Y in FIG. 9C.

In use, as shown in FIG. 9A, the guide catheter 110 is inserted through the cardiovascular system so that its distal end portion 116 is disposed within the aortic complex including the ascending aorta 512, aortic arch 504, and the descending aorta 502. FIG. 9A–9D are sectional views of the cardiovascular system 500 as seen from a left anterior oblique (LAO) viewpoint as seen by a physician via fluoroscopy. The guide catheter 110 is typically inserted into the cardiovascular system 500 at a femoral artery (not shown) with a stiffening wire (not shown) extending through the entire length of the lumen of the guide catheter 110. The stiffening wire is of sufficient rigidity to temporarily overcome the curve portions of the guide catheter 110 so that the guide catheter 110 takes on the shape of the stiffening wire as the stiffening wire passes through the cardiovascular system 500. The guide catheter 110 (with the stiffening wire therein) is advanced distally through the cardiovascular system until the straight tip portion 142 of the guide catheter 110 is beyond the great head and neck arteries 506. The guide catheter 110 (with the stiffening wire extending therethrough) forms a relatively smooth curve to extend about the arch of the aorta 504 and down through the ascending aorta 512. Once the straight tip portion 142 of the guide catheter 110 is in position adjacent the right main coronary artery 518, the stiffening wire is removed from within the guide catheter 110 allowing the guide catheter 110 to attempt to resume its relaxed state (preformed) configuration, (the relaxed state shape prior to insertion in the cardiovascular system, as shown in FIGS. 8A–8C).

The guide catheter 110 is advanced distally and further maneuvered until in the orientation shown in FIG. 9A. This orientation (FIG. 9A) corresponds to the proper and preferred positioning of the guide catheter 110 within the cardiovascular system 500 so that the guide catheter 110 can facilitate the advancement and support of a balloon dilatation catheter 160 through the guide catheter 110. As seen in FIG. 9A, the distal portion 116 of the guide catheter 110 is positioned within the aortic complex such that the tertiary curved portion 123 wraps around the arch of aorta 504, hugs against the postero-medial wall 516 of the ascending aorta 512, as well as against a wall of the descending aorta 502. The last (fifth) curved segment 132 (which can be a straight member in an alternate embodiment) of the tertiary curved portion 123 of the guide catheter 110 extends distally from the rest of the tertiary curve portion 123 to press against and be substantially contiguous with the postero-medial wall of the ascending aorta 158 thereby acting as a supportive segment for the guide catheter 110.

As seen in FIG. 9A, a proximal portion of the secondary curved portion 146 extends distally from the last curved segment 132 of the tertiary curved portion 123. Accordingly, the tertiary curve portion 123 and the proximal portion of the secondary curved portion 146 together define a contact portion of the guide catheter 110 for pressing against and substantially contiguous with the postero-medial wall 516 of the ascending aorta 158. From its distal end, the contact portion extends along the ascending aortic postero-medial wall 516 generally above the ostium 524 of the left main coronary artery. A remaining distal portion of the secondary curved portion 146 (beginning with approximately the apex of its pre-insertion, i.e., relaxed state, curvature) extends laterally away from the postero-medial wall 516 of the ascending aorta 512 so that the second straight portion 138 and the straight tip portion 142 together extend laterally across the ascending aorta 512. As seen in FIG. 9A, the straight portion 138 of the guide catheter 110 extends slightly downward as it extends across the ascending aorta 512 from the distal portion of the secondary curve portion 146 near a distal end 517 of the postero-medial wall 516 of the ascending aorta 512. This arrangement causes the distal straight tip portion 142 to be precisely coaxially intubated within the ostium 520 of the right main coronary artery 518 and, at the same time, maintains contact between the heel of the guide catheter 110 and the postero-medial wall 516 to provide superior backup support.

The primary curved portion 140 of the guide catheter 110 is shown in FIG. 9A, resting in its natural relaxed state orientation of about 155°, which causes the straight tip portion 142 of the distal end portion of the guide catheter 110 to extend substantially horizontally (for a lateral take-off) through the ascending aorta 512 until the distal end of the distal straight tip portion 142 intubates coaxially within the ostium 520. The straight portion 138 and the distal straight tip portion 142 (when properly positioned within the aortic complex as shown in FIG. 9A) together define an axis of support extending across the ascending aorta 512 from the distal end 517 along the postero-medial wall 516 of the ascending aorta 512 generally opposite the ostium to the ostium 520.

Figure 2A:
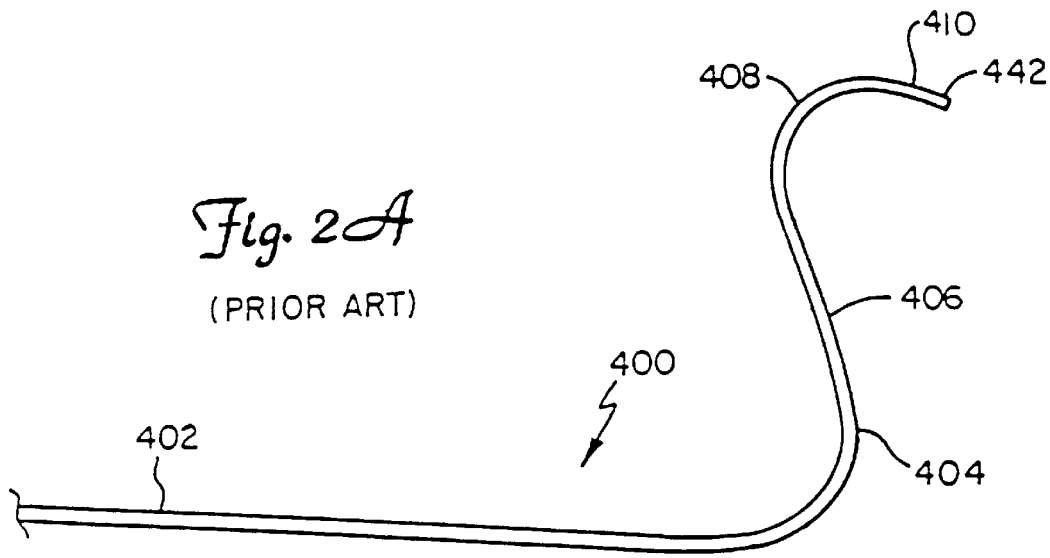
FIG. 2A is a side view of a portion of the Arani-type catheter of the prior art.
Figure 2B:
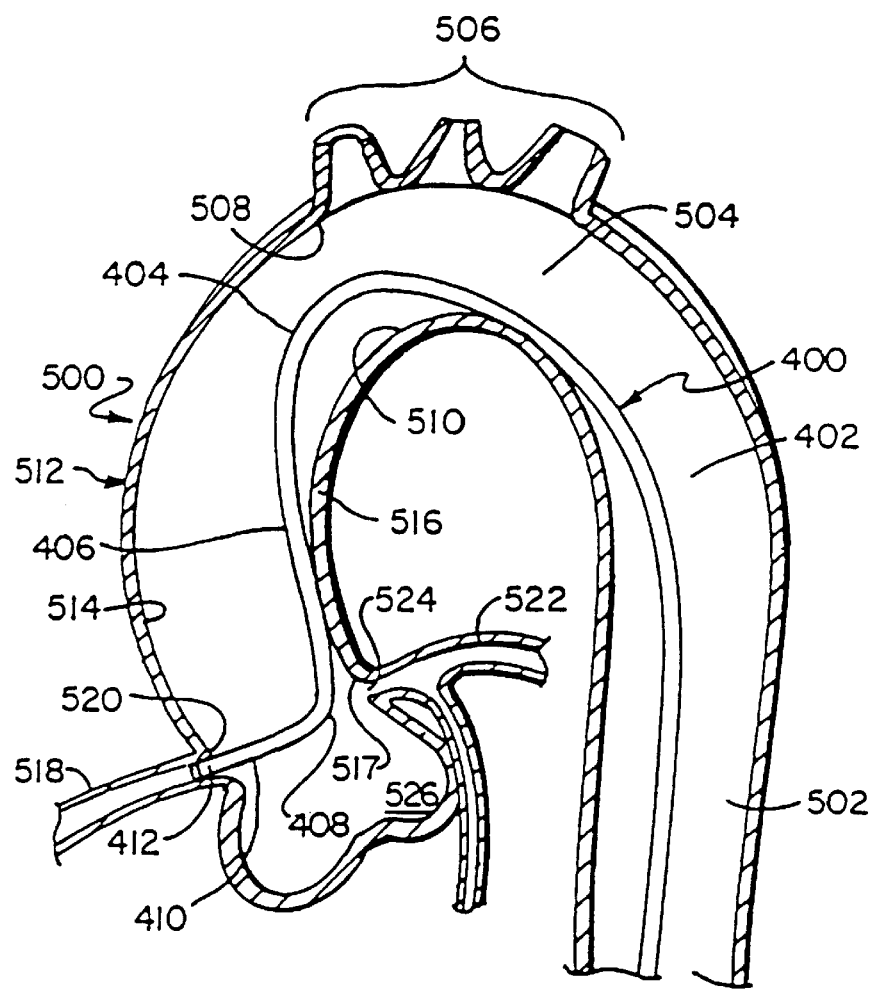
FIGS. 2B and 2C are cross-sectional views taken from a left anterior oblique view of a portion of a cardiovascular system with the Arani-type catheter disposed therein for intubation of the right main coronary artery.
Figure 2C:
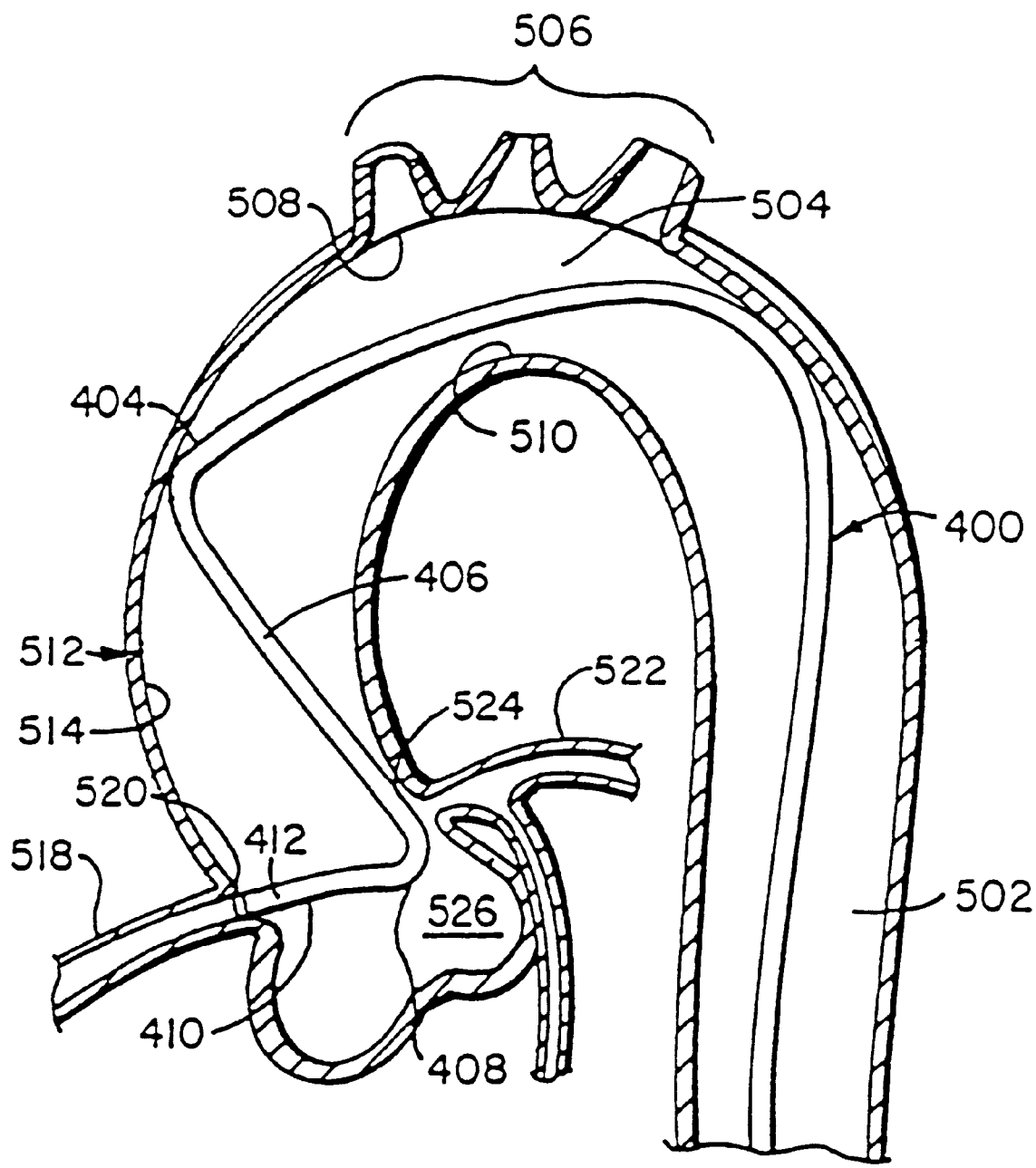

This advantageous orientation of the guide catheter 110 in the cardiovascular system 500 as just described and shown in FIG. 9A is in stark contrast to the disposition of the Arani-style catheter 400 in the cardiovascular system as shown in FIGS. 2A–2C. The Arani catheter 400 when disposed in the fulcrum position can coaxially intubate the ostium 520 but usually does so at the expense of the heel of the catheter losing substantial contact with and therefore backup support from the postero-medial wall 516 as seen in FIG. 2B. Achieving secure intubation of the Arani catheter 400 typically results in the heel of the catheter 400 hanging unsupported in the ascending aorta 512 as seen in FIG. 2B. However, the guide catheter 110 of the present invention as seen in FIG. 9A, establishes coaxial intubation of the tip 142 within the ostium 520 but, unlike the Arani catheter, still maintains substantial positive engagement of the heel of the guide catheter 110 with the postero-medial wall 516 for stable backup support. It is the presence of the mild primary curve portion 140 of the guide catheter 110 disposed midway between the distal end 142 and the apex of the secondary curved segment of the secondary curve portion that insures positive engagement of the heel of the guide catheter 110 with the postero-medial wall 516 and coaxial intubation of the tip 142 within the ostium 520.

One primary feature of the superior (i.e., better) orientation of the guide catheters of the present invention over the prior art catheters is that, when disposed in the aortic complex, a contact portion of the guide catheter 110 is established in a substantially contiguous manner against the aortic wall through the ascending aorta 512, aortic arch 504, and descending aorta 502. This extensive contact between the guide catheter 110 and the inner wall of the portions of the aorta, 502, 504, and 512, respectively, primarily results from the overcurve of the tertiary curve portion 123 pressing against these portions of the aortic anatomy as the tertiary curve portion 123 tries to reassert its natural preinsertion configuration (which has a greater curvature than the curvature of the aortic arch).

Moreover, a distal end of this contact portion is pressed against the postero-medial aortic wall 516 slightly above the ostium 524 of the left main coronary artery 522 at point 517. This positive engagement of the catheter 110 against the wall 516 ensures a primary area of backup support for the guide catheter 110 that is stable and that substantially directly opposes stenotic pushback forces directed outwardly from the ostium 520 of the right main coronary artery 518.

In addition, a distal tip portion of the guide catheters of the present invention (including the second and tip straight portions 138 and 142) when disposed in the aortic complex provide a general axis of support that extends substantially across the ascending aorta 512 from the distal end 517 of the postero-medial wall 516 to the ostium 520 of the right main coronary artery 518. This axis of support generally opposes the axis of the stenotic pushback forces, thereby substantially diminishing the potential for prolapse of the distal tip portion of the guide catheters of the present invention. Furthermore, the distal tip of the guide catheter is aligned essentially coaxially with the ostium 520 of the right main coronary artery 518.

The catheter of the present invention also has the advantage of deep intubation with precise coaxial alignment in the ostium 520 of the right main coronary artery 518. This is significant because the right main coronary artery 518 is frequently smaller than the left main coronary artery 522. Accordingly, a catheter must be precisely configured to permit both deep intubation and coaxial alignment. The guide catheter 110 of the present invention can be advanced from its most conventional use position (FIG. 9A) to the position shown in FIG. 9B where the tip 142 has been advanced further into the ostium 520. This is accomplished by distally advancing the guide catheter 110, thereby causing the secondary curve portion 146 to drop lower in the ascending aorta 512 and the primary curve portion 140 to tend to straighten (although usually not completely) as the tip 142 becomes further intubated in the ostium 520 (this is further accentuated when the guide catheter 110 includes the intermediate flexibility portion 154). This means that the tip has effectively lengthened so that even after deeper intubation, the guide catheter 110 can still bridge the distance from the ostium 520 to the postero-medial wall 516 of the ascending aorta 512. The effective tip length now includes both the straight tip portion 142, primary curve portion 140 and straight tip portion 138, as well as a distal portion of the secondary curve portion 146.

As shown in FIG. 9B, this maneuver can be achieved without the secondary curve portion 146 of the guide catheter 110 dropping below the level of the ostium 524 of the left main coronary artery 522. In particular, the apex of the secondary curve portion 146 remains substantially directly across from the ostium 520 of the right main coronary artery 518 while the proximal portion of the secondary curve portion 146 extends upward along and contacts the postero-medial wall 516 of the ascending aorta. The supportive fifth curved segment 132 of the tertiary curve portion 123 continues to press against the postero-medial wall 516 of the aorta 512 (because of the overcurve of the tertiary curve portion 123 attempting to reassert its preinsertion orientation) to anchor the catheter 110 across from the ostium 520 for providing direct and stable backup support. The remainder of the tertiary curve portion 123 "hugs" and wraps around the aortic arch 504 to prevent slippage of the catheter and maintain stability of the backup support provided along the postero-medial wall 516 of the ascending aorta 512.

The adaptation of the catheter of the present invention to allow for deeper intubation without losing support from the postero-medial wall 516 of the ascending aorta 512 is unique. This is just one aspect of the catheter of the present invention that makes this catheter convertible for many uses in catheterizing the right main coronary artery.

In addition, the presence of the tertiary curve portion provides a gradual bend in the guide catheter (as opposed to the relatively severe bends in an Arani-style guide catheter) when disposed in the aortic complex, thereby allowing a fuller transmission of distal pushing forces through the guide catheter 110. Moreover, the mild obtuse angle (about 160°) of the primary curve portion 140 of the guide catheter 110 and the long distal straight portion 142 cause the distal tip portion 142 to align substantially coaxially within the ostium 520 of the right main coronary artery 518. The distal straight portion 142 also maintains the primary curve portion 140 within the ascending aorta 512 outside of the ostium 520 of the right main coronary artery 518 to provide backup support.

The tertiary curve 123 of the guide catheter 110 has a curvature greater than the curvature of the aortic arch 502. Thus, when the guide catheter 110 is maneuvered into the aortic complex with the tip 142 intubated in the ostium 520, the tertiary curve portion 123 attempts to reassert its original configuration but is prevented from doing so by the inner postero-medial wall 516 of the ascending aorta 512 and the floor 510 of the aortic arch 504, which in combination, have a lesser degree of curvature than the tertiary curve portion 123. Accordingly, the distal portion of the tertiary curve portion 123 pushes inward against the postero-medial wall 516 of the ascending aorta 512. This tension in the guide catheter 110 increases the stability of guide catheter 110 and accentuates backup support because the secondary curve portion 146 of the guide catheter 110 is urged against the postero-medial wall 516 of the ascending aorta 512 just above the ostium 524 of the left main coronary artery 522. This effectively anchors the distal portion 116 of the guide catheter 110 across from the right coronary ostium 520 and substantially diminishes slippage of the guide catheter 110 along the wall of the ascending aorta when resisting stenotic pushback forces.

The primary curve portion 140 of the guide catheter 110 also greatly facilitates easy and accurate intubation of the tip portion 142 within the ostium 520 when initially advancing the guide catheter 110 into the ascending aorta 512. The primary curve portion 140 (as opposed to a quite long straight portion) facilitates directing the tip 142 to the ostium 520 while only requiring minimal rotation and/or up and downward movement of the tip 412 to coaxially intubate the ostium 520.

Moreover, the interaction of the particular configuration of the preformed curves in the distal portion 116 of the guide catheter 110 places the distal portion 116 of the guide catheter 110 in automatic engagement with the postero-medial wall 516 of the ascending aorta and the wall of the aortic arch 502. The guide catheters of the prior art (i.e., Arani) require some (pulling) of the guide catheter to achieve substantial contact with the postero-medial wall 516 of the ascending aorta 512 and wall 510 of aortic arch 504. Moreover, despite this contact, extra backup support is not obtained because the heel of the Arani catheter 400 does not maintain contact with the postero-medial wall 516 as the tip of the Arani catheter 400 is substantially intubated in the ostium 520 in the fulcrum position as shown in FIG. 2B.

Figure 9C:
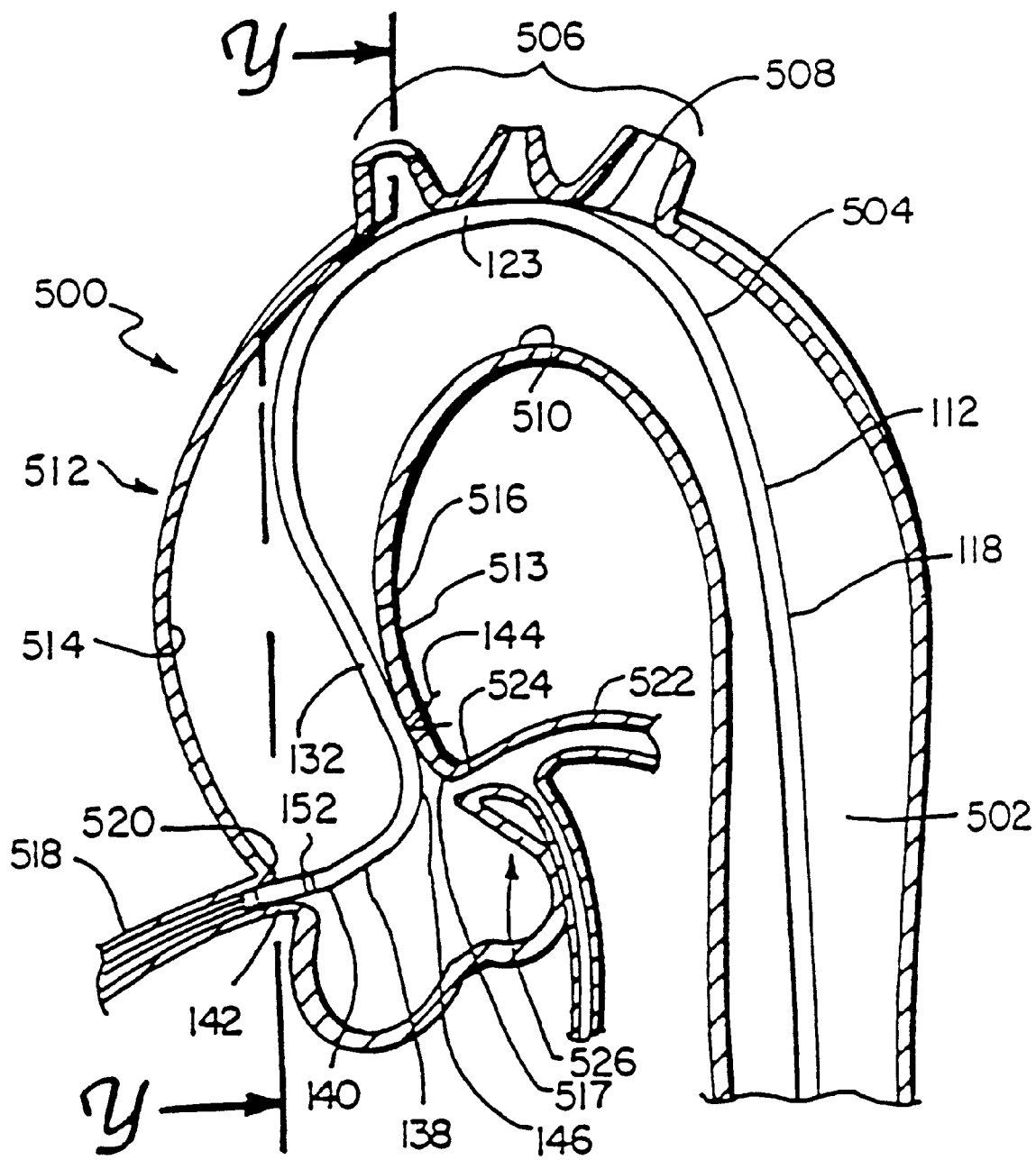

The inventive guide catheter 110 can be advanced to yet another operative orientation from that shown in FIGS. 9A and 9B in order to accentuate backup support for a balloon catheter being advanced distally through the guide catheter 110. As seen in FIG. 9C, the guide catheter 110, while the tip 142 remains deeply intubated within ostium 520 and the fifth supportive segment 132 of tertiary curve portion 123 continues to press against the postero-medial wall 516 of the ascending aorta 512, the remaining proximal portions of the guide catheter 110 are manipulated to alter the orientation of guide catheter 110 to provide further backup support when advancing a balloon catheter through the guide catheter 110 across a tight stenosis. It should be noted that the orientation of the guide catheter 110 shown in FIGS. 9A–9B provides more than adequate backup support for advancing a balloon catheter through the guide catheter 110 in about eighty percent of all angioplasty cases. The orientation shown in FIG. 9C is for more extreme cases, about ten percent, that require even greater backup support than already attainable with the inventive guide catheter 110.

The orientation of FIG. 9C is achieved by further distally advancing shaft 112 of the guide catheter 110 such that the portions of the guide catheter 110 proximal of the supportive segment 132 are lifted away from the postero-medial wall 516 of the ascending aorta 512 and the floor 510 of the aortic arch 504 and pushed upwardly to contact and rest against the roof 508 of the aortic arch 504 in a substantially contiguous fashion. In this orientation, the contact between the portions of the tertiary curve portion 123 against the roof 508 of the aortic arch 504 assist in further maintaining the position of the supportive segment 132 of the tertiary curve portion 123 against the ascending aortic postero-medial wall 516 and the apex of the secondary curve portion 146 adjacent the distal end 517 of the postero-medial wall 516. This maintains the primary area of support for the guide catheter 110 generally opposite the right coronary ostium 520 as was true for the orientations of the catheter shown in FIGS. 9A–9B.

In the advantageous orientation shown in FIG. 9C of the guide catheter 110 of the present invention, the primary curve portion 146 of the guide catheter 110 retains its smooth gradual curvature from the postero-medial wall 516 across the ascending aorta to direct the tip portion 142 to be coaxially intubated within ostium 520. Moreover, the guide catheter 110, as shown in the operative orientation of FIG. 9C, has no sharp bends which cause the several undesirable results seen in previous catheters such as the Arani-style guide catheters. In particular, the lack of sharp bends greatly accentuates transmission of pushing forces of a therapeutic device through the guide catheter 110 in the orientation of FIG. 9C and helps avoid kinking of the shaft of the device through any such sharp bends. In addition, the lack of sharp bends in the guide catheter 110 greatly facilitates any further distal tip manipulations that might be required for adjusting the position of the guide catheter 110 to create any particular desired effect in angulating or maintaining the guide catheter 110 in position during advancement of a therapeutic device.

A particular feature of the operative orientation of FIG. 9C is the supportive segment 132 of the tertiary curve portion 123 which continues to press against the postero-medial wall 516 to anchor the guide catheter 110 and acts as a portion of a rod or column of support between the roof 508 of the aortic arch 504 and the apex of the secondary curve portion 146 (which is maintained generally opposite the ostium 520 of the right main coronary artery 518). Note that even though the tertiary curve portion 123 has lifted off of the floor of the aortic arch, the full extent of the guide catheter 110 still provides a gradual smooth curvature throughout the aortic arch to maximize, or to the extent possible, mimic the gradual curvature of the aortic arch. One additional feature of the orientation of the guide catheter 110 in FIG. 9C that is advantageous as compared to the Arani-style guide catheter 400 shown in the FIGS. 2B and 2C, is that the area of contact between the tertiary curve portion 123 and the roof 508 of the aortic arch 504 is rather extensive (compared to a smaller area of contact for the Arani guide catheter). The greater contact area on the roof 508 assists to greatly prevent slippage of the guide catheter 110 during advancement of the balloon catheter therethrough. In addition, in combination with the area of contact provided by the supportive segment 132 pressing against the postero-medial wall 516, this contact with the roof 508 provides two relatively large areas of firm and stable support for the guide catheter 110 (in contrast to the relatively small points of contact provided by the Arani catheter 400). This further insures stability (i.e., preventing slippage) of the guide catheter 110 while providing enhanced backup support.

The orientation of the catheter in FIG. 9C further illustrates the convertibility of the guide catheter 110 of the present invention from the various positions shown in FIGS. 9A, 9B, and 9C. All of these positions provide tremendous backup support for advancing a balloon catheter, yet in slightly different capacities, while taking advantage of several distinct features of the guide catheter 110, including the mild obtuse angle primary curve portion 140, the support segment 132 of tertiary curve portion 123 and the "overcurved" nature of the tertiary curve portion 123. Moreover, for all of these orientations shown in FIGS. 9A, 9B and 9C, the tip 142 of the guide catheter 110 is conveniently intubatable within the ostium 520 without any significant rotation of the guide catheter 110 when initially advanced into the aortic complex and the ascending aorta 512.

Figure 9D:
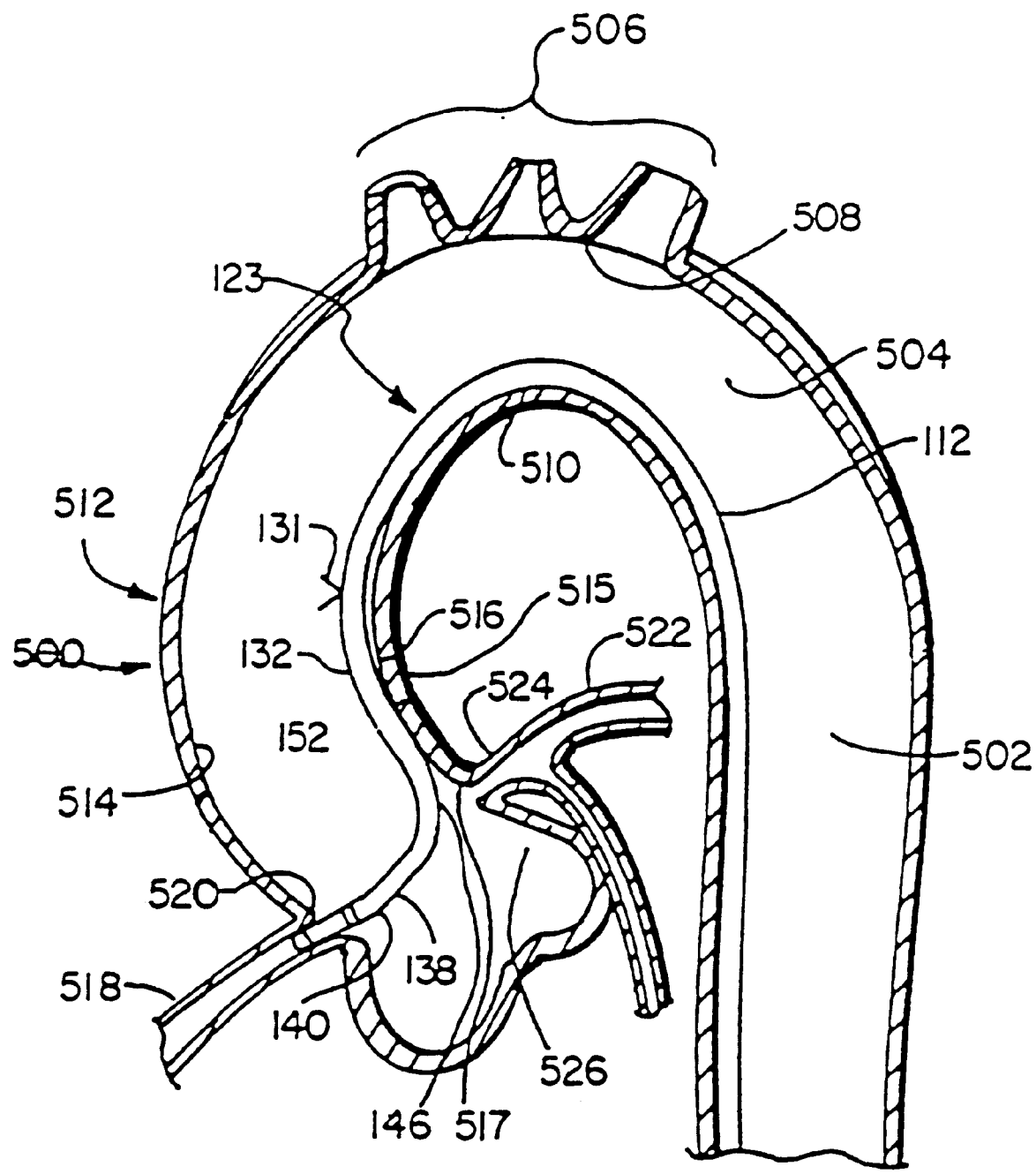

FIG. 9D illustrates a further orientation of the guide catheter 110 of the present invention for a special application in which the lower portion of the ascending aorta 512 has an extensive bend, causing a greater curvature in the ascending aorta 512 and making the right main coronary artery 518 even more difficult to intubate and to provide suitable backup support. This "exit bend" of the ascending aorta 512 occurs about one -to two inches above the aortic valve and is a pronounced medial curvature of the ascending aorta as shown in FIGS. 9A–9C at 513. However, in some patient anatomies (typically older patients or patients with chest deformities), the "exit bend" of the ascending aorta is more pronounced. An example of a pronounced exit bend is illustrated in FIG. 9D at 515. This pronounced exit bend at 515 creates additional challenges for a guide catheter to traverse this anatomical variation and to still provide superior stable backup support for angioplasty or the manipulation of other therapeutic devices.

The guide catheter 110 of the present invention is configured to conveniently adapt to this anatomical variation and provide more than adequate backup support as was described for FIGS. 9A, 9B and 9C. All of the orientations shown for FIGS. 9A–9C are obtainable in the anatomy shown for FIG. 9D. FIG. 9D illustrates that the "overcurved" nature of the tertiary curve portion 123 readily adapts to an overcurved anatomy of the aortic arch 504 and ascending aorta 512 (particularly the postero-medial wall 516). The overcurved tertiary curve portion 123 allows the distal portion 116 of the guide catheter 110 to reach around the extensive curvature of the ascending aorta 512 even with the pronounced exit bend and still readily intubate the ostium 520. As was seen in the orientations of FIGS. 9A–9C, the primary support generally opposite the ostium 520 is maintained in the region 517 of the postero-medial wall 516 by the supportive segment 132, and substantially contiguous contact is maintained between the remaining proximal portions of tertiary curve portion 123 and the ascending aorta 512 and the aortic arch 504.

Figure 9E:
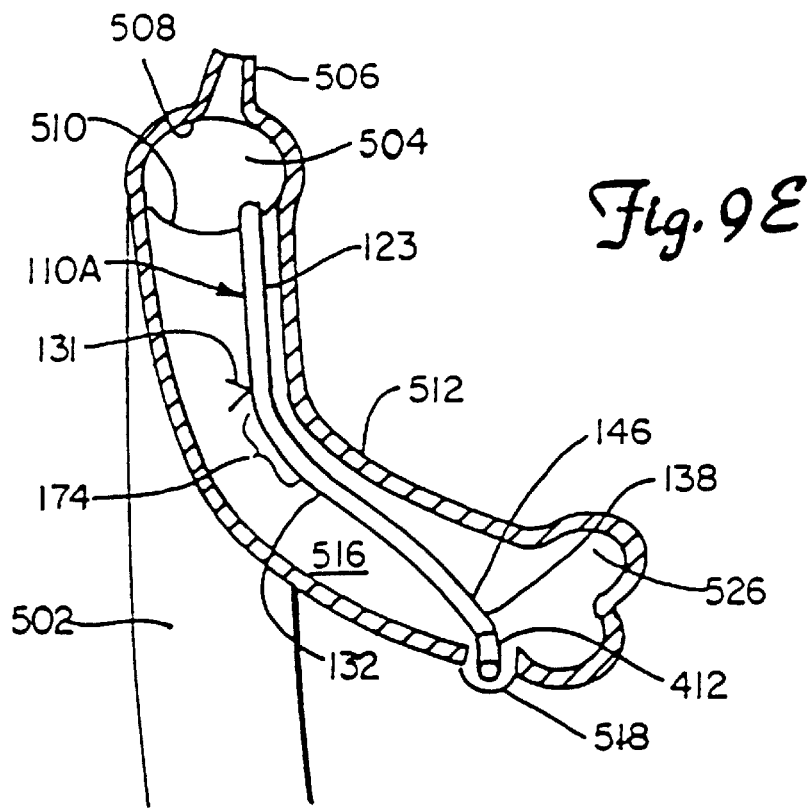

FIG. 9E illustrates the modified guide catheter 110A shown in FIG. 8C in use through the aortic system as viewed from an anterior posterior viewpoint as seen by a physician via fluoroscopy. The modified guide catheter 110A is especially suited for patient anatomies in which the exit bend 515 is very pronounced. As shown in FIG. 8C, the guide catheter 110A extends distally from the plane of the third segment 174 into the plane of the straight portion of the fourth segment 176 to mimic the angled orientation of the plane of the ascending aorta 512 as shown in FIG. 9E. As seen in FIG. 9E, this multiplane, i.e., three dimensional, bending of the guide catheter 110A allows the guide catheter 110A in the distal portion 116 to better trace the three dimensional path of the ascending aorta 512 as it extends toward the heart, achieving an almost perpendicular (i.e., horizontal) orientation relative to the vertical orientation of the descending aorta 502. FIG. 9E represents the position of the guide catheter 110A in the same general orientation as in FIGS. 9A, 9B and 9D (and accordingly the heel of the catheter 110A presses against the postero-medial wall 516). As shown, the location at which the third segment 174 extends within the ascending aorta 512 generally corresponds to the initial curvature of the ascending aorta 512 toward the heart. This allows the distal tip portion 142 of the guide catheter 110A to properly angulate and mimic the orientation of the ascending aorta 512 and thereby enhance proper intubation of the right main coronary artery 518.

Figure 9F:
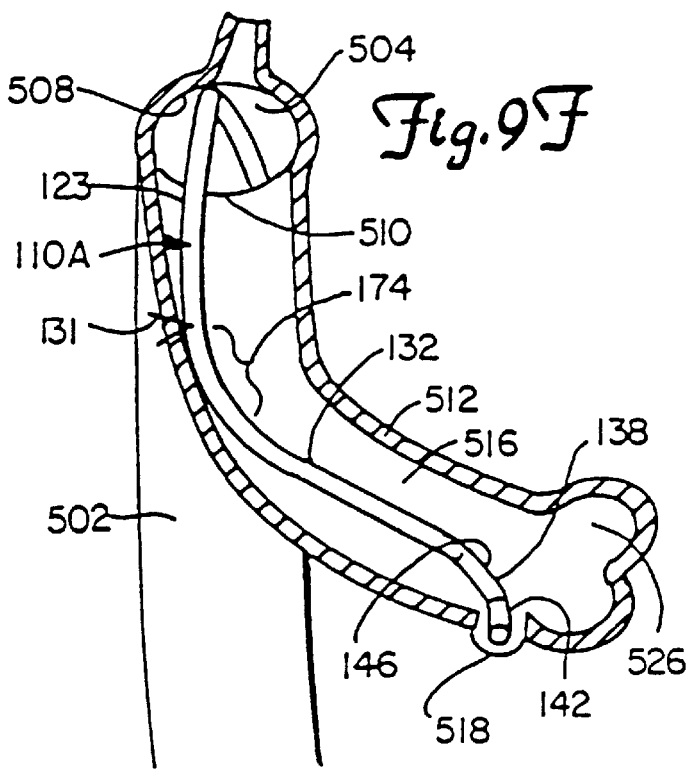

FIG. 9F shows an orientation of the guide catheter 110A in which the general orientation as in FIG. 9C is achieved. FIG. 9F is the cardiovascular system 500 as seen under fluoroscopy from the anterior posterior viewpoint. In the orientation of FIG. 9C, the tertiary curve portion 123 substantially contacts the roof 508 of the aortic arch 504. However, in this orientation for multiplane three dimensional guide catheter 110A, the third segment 174 is pushed against a wall of the ascending aorta 512 about the point where the curvature of the ascending aorta 512 toward the heart begins. This provides an additional area of support for the guide catheter 110A against the wall of the ascending aorta 512 in addition to the primary area of support provided by supportive segment 132 pressing against the postero-medial wall 516 of the ascending aorta 512 and the support provided by contact of the tertiary curve portion 123 along the roof 508 of the aortic arch 504. Thus, it can be seen that the advantageous features of the inventive guide catheter can be employed in extreme anatomical variations such as those shown in FIGS. 9E and 9F by modifications of the configuration of the guide catheter, including providing a multiplane distal portion and by using orientations such as shown by FIG. 9C to provide even more support for the guide catheter in those extreme anatomical situations requiring extra backup support.

Figure 10B:
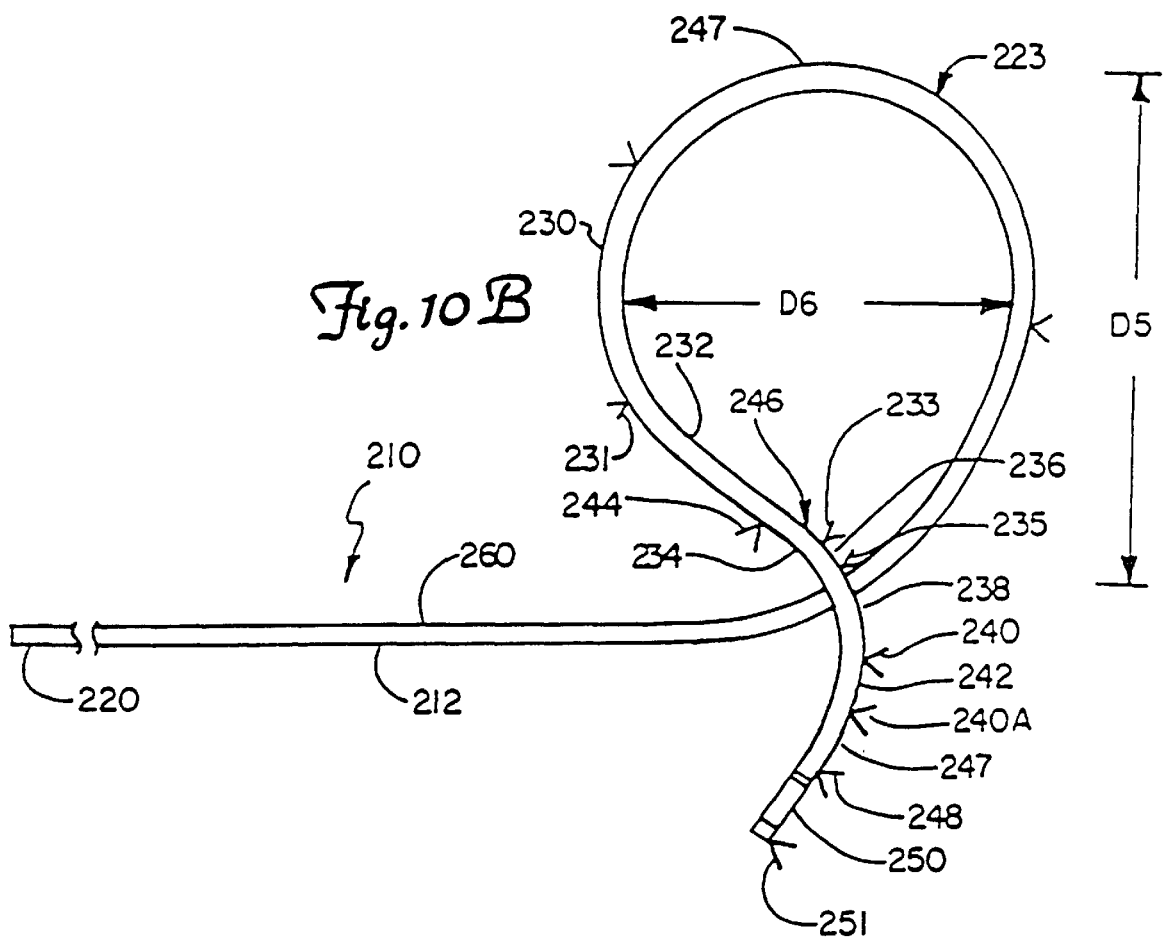

Another embodiment of the present invention is a guide catheter 210, illustrated in FIGS. 10A–10B in its relaxed state prior to insertion in a cardiovascular system. From its proximal end 220 to point 244 at the end of tertiary curve portion 223, the shaft 212 of the guide catheter 210 is formed the same as guide catheter 110 described above. It differs from guide catheter 110 in its distal portion, distal of the tertiary curve portion 223. The distal portion 216 of the guide catheter 210 includes the tertiary curved portion 223, a secondary curved portion 246, and a distal tip portion further includes a second straight portion 242, a primary curved portion 247, and a straight tip portion 250.

The secondary curved portion 246 extends distally from the distal end of the tertiary curve portion 223 from the point 244 to a point 240 along the catheter shaft 212. The second straight portion 242 extends distally from the point 240 to a point 244 along the catheter shaft 212. The primary curved portion 247 extends distally from the point 244 to a point 248 along the catheter shaft 212. The straight tip portion 250 extends distally from the point 248 to a point 251 which defines a terminal end of the catheter 210.

As mentioned, the catheter shaft 212, through the tertiary curve portion 223, is the same as previously described. The secondary curved portion 246, however, is different and is preferably comprised of three discrete segments: a first curved segment 234, an intermediate straight segment 236, and a second curved segment 238. The first curved segment 234 forms an arc of about 20°, has a radius of about 2.0 centimeters, and is about 0.70 centimeters long (from point 244 to point 233 along the catheter shaft 212). The intermediate straight segment 236 extends distally from the distal end of the first curved segment 234 for about 0.5 centimeters (from point 233 to point 235 along the catheter shaft 212). The second curved segment 238 extends distally from the intermediate straight segment 234, forms an arc of about 50°, has a radius of about 1.5 centimeters, and has a length of about 1.3 centimeters (from point 235 to point 240 along the catheter shaft 212).

The second straight portion 242 of the guide catheter 210 extends rectilinearly about 0.70 centimeters from the distal end of the secondary curved portion 246, from the point 240 to a point 240A along the catheter shaft 212. The primary curved portion 247 extends distally from the point 240A to a point 248. The primary curved portion 247 forms an arc of about 25°, has a radius of about 2.0 centimeters, and is about 0.85 centimeters long. The straight tip portion 250 extends distally from the primary curve portion 247 for about 1.35 centimeters. The primary curve portion 247 forms an obtuse angle of approximately 155° between the second straight portion 242 and the straight tip portion 250.

The distance D5 (see FIG. 10B) from the point at which the distal portion 216 overlaps itself to a point diametrically opposite therefrom along the tertiary curve portion 223 is about 7.35 centimeters. The distance D6 in FIG. 10B is about 6.0 centimeters. The distance from the point 147 to the secondary curve portion 246 is about 8.5 to 9.5 centimeters when the catheter 210 is fully disposed in the right main coronary artery 518 (such as, e.g., disposed in FIG. 9A). The length of the catheter 210 between the utmost distal end 251 of the catheter 210 and an apex of the primary curve portion 240 is about 1.8 centimeters. The length of the catheter 210 between the apex of the primary curve portion 240 and an apex of the second curved segment 238 is about 1.8 centimeters. The length of the catheter 210 between the apex of the second curved segment 238 and the apex of the first curved segment 234 is about 1.5 centimeters long.

As shown in FIG. 10A, the guide catheter 210 is constructed of three shaft segments, each with a different degree of flexibility. The guide catheter 210 in FIG. 10A has a first flexibility segment 260 with a Shore D hardness of 63, a second increased flexibility segment 264 with a Shore D hardness of 40, and a third, further increased flexibility tip segment 266 with a Shore D hardness of about 35. A bond ring member 262 is sandwiched between a distal end of the first segment 260 and a proximal end of the second segment 264, and has a hardness of about 51. As shown, the bond ring member 262 is preferably positioned just distal to the primary curve portion 240. In an alternate embodiment, the bond ring member 262 can be positioned proximally of the proximal curve portion 240. Instead of the triple flexibility segment construction, the guide catheter 210 can have a double flexibility segment construction as described for the guide catheter 110. In addition, for both the double and triple flexibility segment constructions of the guide catheter 210, the same materials (e.g., PEBAX® material, TEFLON® material, wire braiding and radiopaque agents) can be used as was described for the guide catheter 110. Moreover, the method of forming the preshaped configuration of the guide catheter 210 is the same as described for the guide catheter 110.

An alternate embodiment of guide catheter 210 extends in multiple planes with a three dimensional distal portion 216 like that of guide catheter 110A as shown in FIG. 8C. The segments of the guide catheter 210A have the same lengths and angles and curvatures as the guide catheter 110A as seen in the top view of FIG. 8C despite the guide catheter 210 having slightly different dimensions for portions 250, 242, and 246 as seen in FIGS. 10A and 10B.

The guide catheter 210 is inserted into the cardiovascular system in the manner previously described for guide catheter 110 and as depicted in FIGS. 9A–9F. The guide catheter 210 assumes the same advantageous orientation within the ascending aorta 512 and ostium 520 of the right main coronary artery 518 as is shown in FIG. 9A–9F (as shown for the guide catheters 110 and 110A). The guide catheter 210, because of its slightly altered construction adjacent its distal end, provides a longer effective tip length for the guide catheter, to aid in extending across the ascending aorta and into the right coronary artery.

A modification of the embodiment shown in FIGS. 10A–10B is especially suited for catheterization of a "Shepherds Crook" anatomical variation of the right main coronary artery. The modification includes altering the distal straight tip portion 250, the primary curve portion 247, and the second straight portion 242. The distal tip portion 250 is lengthened to about 2 centimeters and the second straight portion 242 is shortened to about 0.25 centimeters. The arc of primary curve portion 247 is tightened to about 35° (having a radius of curvature of about 2.0 centimeters) and the length of the arc extended to about 1.2 centimeters. This modification of the guide catheter 210 facilitates intubation of a "Shepherds Crook" formed right main coronary artery which has a severe superior take-off orientation where the artery extends upwardly, for a portion, almost parallel to the ascending aorta 512. Other than these slight modifications of the guide catheter 210 in the three portions 250, 247, and 242, the alternate embodiment for the Sheperds Crook anatomical variation is same as the guide catheter 210 shown in FIGS. 10A and 10B.

Figure 10C:
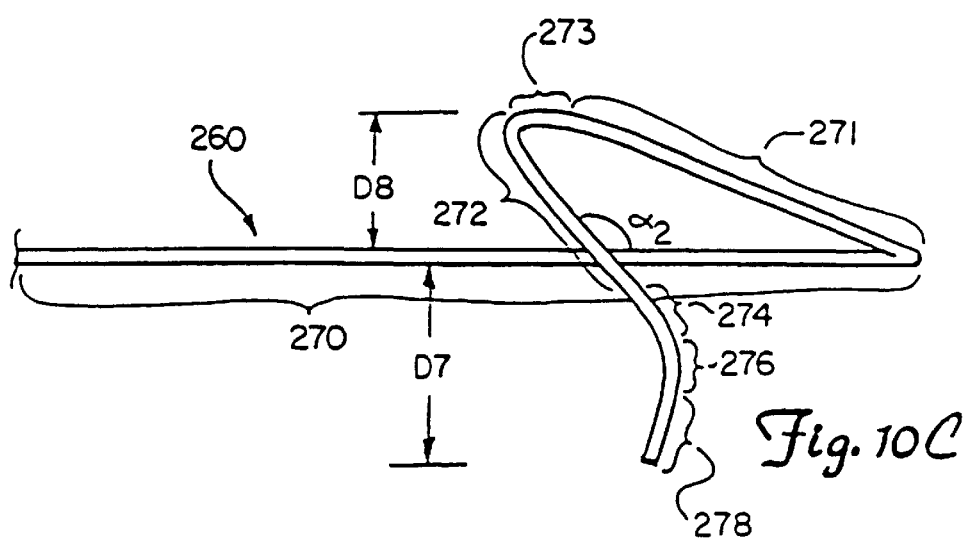
FIG. 10C is a top view of a modified version of the catheter of FIGS. 10A and 10B, as viewed from the top of FIGS. 10A and 10B.

However, the alternate embodiment of guide catheter 210 adapted for the Sheperds Crook variation also can be modified into a multiplane three dimensional embodiment similar to the embodiment shown in FIG. 8C. As seen in FIG. 10C, a three dimensional guide catheter 260 is shown having first, second and third segments 270, 271 and 273 which are the same as segments 170, 172 and 174, respectively as the guide catheter shown in the view of FIG. 8C. Distal of the third segment 273, the catheter 260 has a fourth segment 272 with a proximal portion extending from the third segment 273 and a straight portion with a length of about 2.35 centimeters. The angle between the plane traversed by the third segment 273 and the plane traversed by the straight portion of the fourth segment 272 is about 45°. The fourth segment of catheter 268 crosses over the first segment 270 at about the same angle of 130 degrees (i.e., $\alpha_2$) Extending distally from the fourth segment 272 is a fifth segment 274 having a radius of curvature of about 10 centimeters and forming an arc of about 50 degrees. A sixth segment 276 extends distally from the fifth segment 274 and has a radius of curvature of about 1.0 centimeters and forms an arc of about 60 degrees. A straight seventh segment 278 extends distally from the sixth segment 276 for about 1.1 centimeters. The distances D7 and D8 are the same as the distances D3 and D4, respectively, for the guide catheter shown in FIG. 8C.

Figure 11:
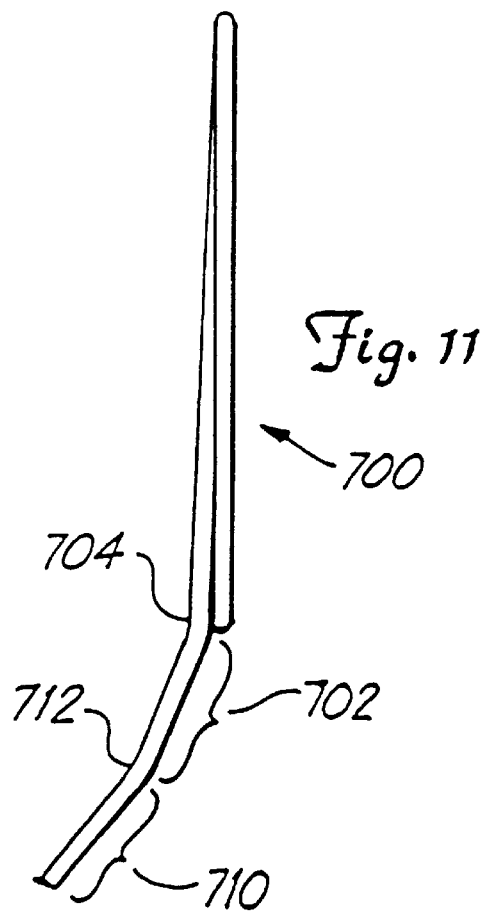
FIG. 11 is an end view of a modified version of the catheter of FIG. 10A, as viewed from the right side of FIGS. 10A and 10B.

FIGS. 11 and FIGS. 12 show additional embodiments of the guide catheter of the present invention which are variations of the basic configuration of the guide catheters shown in FIGS. 8A–8B and 10A–10B. These additional embodiments are especially suited for intubating saphenous bypass grafts of the ascending aorta 512 in the vicinity of the left and right main coronary arteries. A saphenous bypass graft typically involves using a great saphenous vein from the leg as a graft onto the wall of the ascending aorta to bypass an occluded main coronary artery.

The guide catheters 110 and 210 of the present invention can be used for intubating the ostium of a saphenous bypass graft by making relatively slight modifications in the shape of the distal portion of the catheter. FIG. 11 is an end view of a catheter 700, as taken from the right side of a catheter view such as FIG. 10A. The guide catheter 700 is adapted for use in treatment of a left saphenous vein bypass graft. The guide catheter 700 depicted in FIG. 11 corresponds in every capacity to the guide catheter 210 of FIGS. 10A–10B except for the out-of-plane modifications adjacent its distal end. As shown in FIG. 11, the distal portion of the guide catheter 700 is bent out of plane consecutively at two different angles. The first out of plane portion 702 extends at angle of about 20 degrees away from the first plane of the catheter 700 at a bend 704. The bend 704 is located approximately at the apex of a second curved segment of a secondary curve portion of the catheter body (i.e., at the apex of the second curved segment 238 of the secondary curve portion 246 for the guide catheter 210). The second out of plane portion 710 extends from the first out of plane portion 702 at angle of about 40 degrees relative to the first plane of the catheter 700 at a bend 712. The bend 712 is located approximately at the apex of a primary curve portion of the catheter body (i.e., at the apex of the primary curve portion 247 for the guide catheter 210). The configuration of the guide catheter 700 permits coaxial intubation and provides backup support for an angioplasty procedure through a left saphenous vein bypass graft in a cardiovascular system. Because the guide catheter 700 has the same basic structure as the guide catheter 210, the guide catheter 700 enjoys all the advantages of the catheter 210 when deployed in the cardiovascular system.

An alternate embodiment of the catheter 700 for use in left saphenous bypass graft has the same out of plane bending as shown in FIG. 11 but also includes modifying the lengths of the following portions of the guide catheter 210 as seen in FIG. 10B: a second straight portion (like the second straight portion 242 of the guide catheter 210) is lengthened to about 1.20 centimeters and a distal tip straight portion (like straight tip portion 250 of the guide catheter 210) is lengthened to about 1.85 centimeters.

Figure 12A:
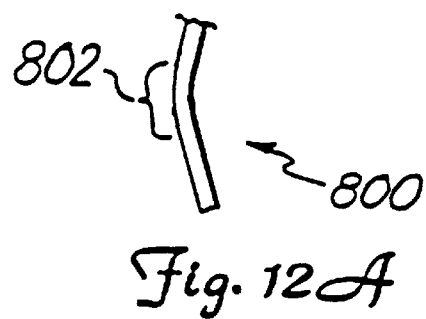
FIG. 12A is a side view of a modified version of the distal portion of the catheter of FIG. 10A.
Figure 12B:
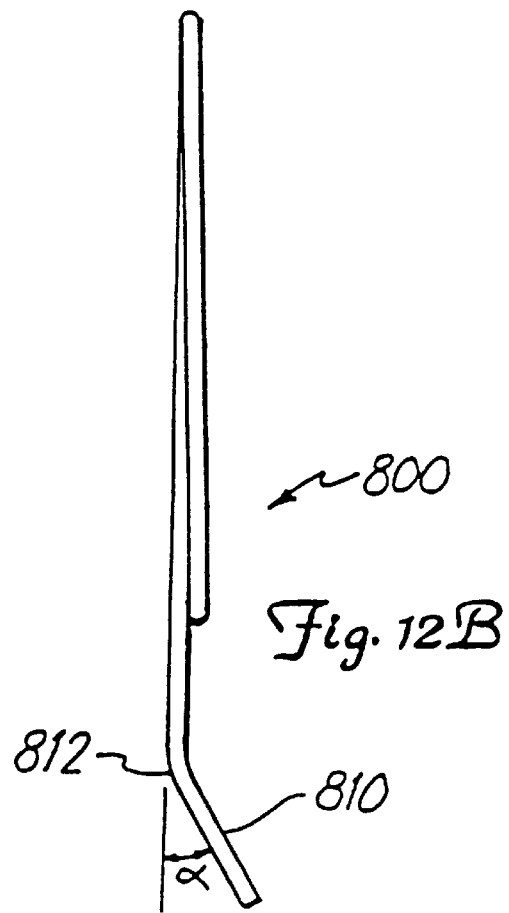
FIG. 12B is an end view of the modified version catheter of FIG. 12A, as seen from the right side of FIG. 12A.

A guide catheter 800 is shown in FIGS. 12A and 12B, and is adapted for use in treatment of a right saphenous vein bypass graft. FIG. 12A is a side view like FIG. 10A but only showing the distal end portion of the guide catheter 800. FIG. 12B is an end view of the guide catheter 800, as taken from the right side of a catheter view such as FIG. 10A. The guide catheter 800 depicted in FIG. 12A corresponds in every capacity to guide catheter 210 shown in FIG. 10A except for the out-of-plane modifications adjacent its distal end (FIG. 12B) and a reverse orientation of primary curve portion 802 (as compared to primary curve portion 247 in FIG. 10A). The interior of the arc of the primary curve portion 802 is disposed oppositely from the orientation of the primary curve portion 247 shown in FIG. 10A. The primary curve portion 802 the guide catheter 800 has a radius of curvature of 2.0 centimeters and forms an arc of about 25 degrees. As shown in FIG. 12B, the distal portion of the catheter is bent out of plane in one plane. The first out of plane portion 810 extends at an angle of about 30 degrees away from the first plane of the catheter 800 at a bend 812. The bend 812 is located approximately at the apex of the primary curve portion 802 of the catheter body (i.e., at the apex of the primary curve portion 247 of the guide catheter 210). The configuration of the guide catheter 800 permits coaxial intubation and provides backup support for an angioplasty procedure through a right saphenous vein bypass graft in a cardiovascular system. Because the guide catheter 800 has the same basic structure as the guide catheter 210, the catheter 800 enjoys all the advantages of the catheter 210 when deployed in the cardiovascular system.

It is thus seen that the guide catheters of the present invention are specifically configured for more precise coaxial alignment with a selected (e.g., right main) coronary artery in the cardiovascular system without the need to rotate the catheter. Also, the guide catheters of the present invention provide improved support and guidance of associated therapeutic devices, such as balloon catheters, during angioplasty. Further, the guide catheters of the present invention form relatively small angles when inserted in the cardiovascular system, thus minimizing the dissipation of axial forces during use. In addition, the inventive guide catheters can be formed so as to maintain these characteristics even after warming to body temperature or when the aortic arch is overcurved.

It is understood that several variations may be made in the foregoing without departing from the scope of the invention. For example, the catheters embodied in the present invention are not limited for use as guiding catheters but can have other uses for treatment of the cardiovascular system, such as use as diagnostic, balloon, laser and atherectomy catheters, etc. The catheters of the present invention may also be introduced to the aorta via the brachial or axillary artery in addition to the femoral artery. Further, the present invention can be used to form catheters for use in cases of posterior take-off of the right coronary artery. Also, the specific lengths and angles of the specific examples of the catheters of the present invention set forth above can be varied within the scope of the invention. In addition, although the angles A1 (FIG. 4B) and A4 (FIG. 6B) have been shown at the apex of the curved portions 54 and 82, it is understood that they could be located at other portions of the curved portions 54 and 82. Moreover, it is understood that, instead of the well defined lengths and angles shown and described in the above examples, the bent distal end portion of the a catheters of the present invention can form more smoother curves within the scope of the invention.

It should also be understood that the embodiments of FIG. 3A–7A can be made with the materials and by the technique described for the embodiments of FIG. 8A and 10A. Moreover, features of the various embodiments (3A–8A, 8C, 10A, 10C, 11, and 12A–12B) can be combined with each other to achieve additional optimal combinations of catheter configurations within the scope of the present invention.

Other modifications, changes and substitutions are intended in the foregoing disclosure and in some instances some features of the invention will be employed without a corresponding use of other features. Accordingly, it is appropriate that the appended claims be construed broadly and in a manner consistent with the scope of the invention.

What is claimed is:

1. A guide catheter for use in treatment of a selected coronary artery accessed from an aorta including a descending aorta, an aortic arch, an ascending aorta and the ostium of the selected coronary artery, the guide catheter comprising:

a hollow, flexible tubular body having a proximal end and a distal end; and means for engaging the tubular body with the wall of the ascending aorta and to the wall of the aortic arch when the distal end is generally coaxially aligned relative to the ostium of the selected coronary artery; the means for engaging including a primary curve proximal the distal end, a secondary curve proximal the primary curve and a tertiary curve proximal the secondary curve.

* * * * *